United States Patent
Choi et al.

(10) Patent No.: US 12,303,490 B2
(45) Date of Patent: May 20, 2025

(54) COMPOSITIONS AND METHODS FOR SUPPRESSING AND/OR TREATING NEURODEGENERATIVE DISEASES AND/OR A CLINICAL CONDITION THEREOF

(71) Applicant: CK Regeon Inc., Seoul (KR)

(72) Inventors: Kang-Yell Choi, Seoul (KR); Minguen Yoon, Seoul (KR); Soung-Hoon Lee, Seoul (KR)

(73) Assignee: CK Regeon Inc., Seoul (KR)

( * ) Notice: Subject to any disclaimer, the term of this patent is extended or adjusted under 35 U.S.C. 154(b) by 735 days.

(21) Appl. No.: 17/642,838

(22) PCT Filed: Nov. 3, 2020

(86) PCT No.: PCT/IB2020/060319
§ 371 (c)(1),
(2) Date: Mar. 14, 2022

(87) PCT Pub. No.: WO2021/090172
PCT Pub. Date: May 14, 2021

(65) Prior Publication Data
US 2022/0378741 A1  Dec. 1, 2022

Related U.S. Application Data

(60) Provisional application No. 62/930,022, filed on Nov. 4, 2019.

(51) Int. Cl.
*A61K 31/404* (2006.01)
*A61P 25/16* (2006.01)
*A61P 25/28* (2006.01)

(52) U.S. Cl.
CPC ............ *A61K 31/404* (2013.01); *A61P 25/16* (2018.01); *A61P 25/28* (2018.01)

(58) Field of Classification Search
CPC ..... A61K 31/404; C07D 403/04; A61P 25/16; A61P 25/28; A61P 25/14
See application file for complete search history.

(56) References Cited

U.S. PATENT DOCUMENTS

| | | | |
|---|---|---|---|
| 8,716,220 B2 | 5/2014 | Tezapsidis et al. | |
| 11,459,311 B2 | 10/2022 | Choi et al. | |

(Continued)

FOREIGN PATENT DOCUMENTS

| | | |
|---|---|---|
| CN | 101023944 A | 8/2007 |
| EP | 3 705 474 A1 | 9/2020 |

(Continued)

OTHER PUBLICATIONS

Meijer et al. Journal of Medicinal Chemistry 2004 47 (4), 935-946. (Year: 2004).*

(Continued)

*Primary Examiner* — Joseph K McKane
*Assistant Examiner* — Ashli Ariana Chicks
(74) *Attorney, Agent, or Firm* — NSIP Law

(57) ABSTRACT

Therapeutic compositions comprising one or more agents that inhibit CXXC5-DVL interface and/or that enhance the activity of GLP-1, and methods of administering those therapeutic compositions to model, treat, reduce resistance to treatment, prevent and diagnose a condition/disease associated with neurodegenerative diseases or a related clinical condition thereof, are disclosed.

11 Claims, 12 Drawing Sheets

(56) References Cited

U.S. PATENT DOCUMENTS

2010/0068303 A1 3/2010 Yu
2010/0331327 A1 12/2010 Meijer et al.

FOREIGN PATENT DOCUMENTS

| KR | 10-1932668 B1 | 12/2018 |
|---|---|---|
| WO | WO 00/61555 A1 | 10/2000 |
| WO | WO 2005/041954 | 5/2005 |
| WO | WO 2005/107466 A1 | 11/2005 |
| WO | WO 2007/099402 A2 | 9/2007 |
| WO | WO 2010/013168 A1 | 2/2010 |
| WO | WO 2012/065065 A9 | 5/2012 |
| WO | WO 2013/142817 A2 | 9/2013 |
| WO | WO 2018/183631 A1 | 10/2018 |
| WO | WO 2018/183631 A8 | 10/2018 |
| WO | WO 2020/079569 A1 | 4/2020 |
| WO | WO 2020/079570 A1 | 4/2020 |

OTHER PUBLICATIONS

Knockaert, Marie, et al. "Independent actions on cyclin-dependent kinases and aryl hydrocarbon receptor mediate the antiproliferative effects of indirubins." *Oncogene* 23, No. 25 (Apr. 12, 2004): pp. 4400-4412.

Gaboriaud-Kolar, Nicolas, et al. "Natural-based indirubins display potent cytotoxicity toward wild-type and T315l-resistant leukemia cell lines." *Journal of natural products* 79. No. 10 (Oct. 11, 2016): pp. 2464-2471.

Kosuge, Yasuhiro, et al. "Indirubin derivatives protect against endoplasmic reticulum stress-induced cytotoxicity and down-regulate CHOP levels in HT22 cells." Bioorganic & Medicinal Chemistry Letters vol. 27. Issue 23 (2017). pp. 5122-5125.

Meijer, Laurent, et al. "GSK-3-Selective Inhibitors Derived from Tyrian Purple Indirubins." *Chemistry & biology* vol. 10. Issue 12 (2003). pp. 1-12.

Nisha, Chaluveelaveedu Murleedharan, et al. "Docking and ADMET prediction of few GSK-3 inhibitors divulges 6-bromoindirubin-3-oxime as a potential inhibitor." *Journal of Molecular Graphics and modelling* vol. 65 (2016). pp. 1-8.

Zhang, Na, et al. "3D QSAR for GSK-3β inhibition by indirubin analogues." *European journal of medicinal chemistry* vol. 41. Issue 3 (2006). pp. 1-6.

Furuta, Takuya. "The functional diversity and clinical significance of GSK3β in glioma." *Progress in Neuro-Oncology* vol. 25. Issue 1 (2018). pp. 1-9.

\* cited by examiner

COMPOSITIONS AND METHODS FOR SUPPRESSING AND/OR TREATING NEURODEGENERATIVE DISEASES AND/OR A CLINICAL CONDITION THEREOF

CROSS REFERENCE TO RELATED APPLICATIONS

This application is a U.S. National Stage Application of International Application No. PCT/IB2020/060139, filed on Nov. 3, 2020, which claims the benefit of U.S. Provisional Application No. 62/930,022, filed Nov. 4, 2019, the entire disclosure of which is hereby expressly incorporated by reference herein.

FIELD

Various aspects and embodiments disclosed herein relate generally to modelling, treating, reducing resistance to a treatment, preventing, and diagnosing of conditions/diseases associated with neurodegenerative diseases or a related clinical condition thereof. Embodiments include compositions and methods for treating the conditions/diseases, comprising providing to a subject at least one therapeutically effective dose of a composition disclosed herein. Other embodiments include methods for altering and/or enhancing the activity of the GLP-1 in a subject.

BACKGROUND

Neurodegenerative diseases including Alzheimer's disease (AD) and Parkinson's disease (PD) may be found in the elderly population and the number of patients may increase exponentially with aging society. Early-onset of neurodegenerative diseases in the young are not uncommon. Alzheimer's disease, the most common form of dementia among older adults, is an irreversible degeneration of the brain that causes disruptions in memory, cognition, personality, and other functions that eventually lead to death from complete brain failure. Genetic and environmental factors including diet, activity, smoking, traumatic brain injury, diabetes, and other medical diseases contribute to the risk of developing this form of the disease. Parkinson's disease is the most prevalent form of dementia and is characterized by cognitive insufficiencies and behavioral changes that affect memory and learning abilities, daily functioning and quality of life. Parkinson's disease may be caused by the predominate loss of dopamine-producing neurons in brain.

Some studies have reported the involvement of glucagon-like peptide-1 (GLP-1) in development of neurodegenerative diseases such as Alzheimer's disease and Parkinson's disease. GLP-1 may affect neurological and cognitive functions, as well as its regulatory effect on glucose metabolism. It is postulated that the mechanisms for cognitive impairment include impairment in cerebral insulin signaling, change in amyloid metabolism, accumulation of advanced glycation end products, and oxidative stress. Due to the complexity of the processes involving the regulation of neurodegenerative diseases such as Alzheimer's disease and Parkinson's disease, the development of a new treatment regimen(s) is much needed.

SUMMARY

Given CXXC5's involvement as a negative regulator of GLP-1 and the unexpected overexpression of CXXC5 in the brain of a subject having Alzheimer and/or Parkinson's diseases, it is an attractive target for the development of compounds that can improve these diseases by interfering CXXC5-DVL interface.

Some aspects of the instant disclosure include compounds that interfere with CXXC5-DVL interface and methods of using the same to influence and/or treat neurodegenerative diseases such as Alzheimer's disease and Parkinson's disease in a subject.

Embodiments of the instant application relate to compositions and methods for treating a condition and/or disease associated with neurodegenerative diseases or a related clinical condition in a subject. In certain embodiments, the compositions and methods disclosed herein include suppression of one or more side effects of a therapeutic regime. Other embodiments relate to compositions and methods for treating a subject diagnosed with a disease or having a condition contributed to neurodegenerative diseases, due at least in part by the suppressed expression of active GLP-1 in a subject.

In a first aspect, compositions disclosed herein comprise at least one agent that may act by inhibiting the CXXC5-DVL interface—the interface between CXXC finger protein 5 (CXXC5) and disheveled (DVL)—in a subject. In some embodiments, at least one agent that inhibits CXXC5-DVL interface comprises at least one agent that binds to the PDZ domain of disheveled (DVL) and/or the DVL binding motif, at least one GSK3β inhibitor, at least one GLP-1 analogue, and/or at least one GLP-1 receptor agonist, or a combination thereof.

A first embodiment includes a compound of Formula I for use in a method of treating a condition and/or disease associated with neurodegenerative diseases or a related clinical condition in a subject,

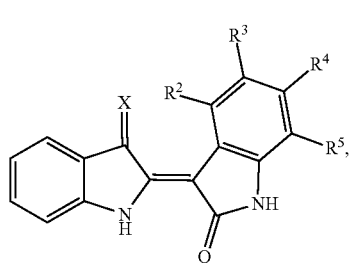

I wherein X is O or N optionally substituted with $R^1$;

$R^1$ is hydrogen, hydroxy, alkyl, alkenyl, or an alkoxy optionally substituted with alkyl, alkenyl, haloalkyl, aryl, or benzyl; or $R^1$ is hydrogen, alkyl, alkenyl, or an alkoxy substituted with butyl, alkenyl, haloalkyl, aryl, or benzyl.

$R^2$ is hydrogen, nitro, halogen, alkyl, alkenyl, haloalkyl, alkoxy, haloalkoxy, or a carboxy.

$R^3$ is hydrogen, nitro, halogen, alkyl, alkenyl, haloalkyl, alkoxy, haloalkoxy, or a carboxy; or $R^3$ is hydrogen, fluorine, iodine, astatine, alkyl, alkenyl, haloalkyl, $OCF_3$, ethoxy, propyloxy, butyloxy, haloalkoxy, or a carboxy, and/or wherein when $R^3$ is bromine or chlorine, $R^4$ is not hydrogen; and/or wherein when $R^3$ is chlorine, $R^4$ is not chlorine.

$R^4$ is hydrogen, nitro, halogen, alkyl, alkenyl, haloalkyl, alkoxy, haloalkoxy, or a carboxy; or $R^4$ is hydrogen, nitro, fluorine, bromine, iodine, astatine, alkyl, alkenyl, haloalkyl, alkoxy, haloalkoxy, or a carboxy; and/or wherein when $R^4$ is chlorine, $R^3$ is not hydrogen or nitro.

$R^5$ is hydrogen, nitro, halogen, alkyl, alkenyl, haloalkyl, alkoxy, haloalkoxy, or a carboxy.

A second embodiment includes the compound according to the compound of the first embodiment, wherein X is O.

A third embodiment includes the compound according to the compound according to the compound of the first embodiment, wherein X is N and $R^1$ is hydroxy or alkoxy optionally substituted with alkyl, alkenyl, haloalkyl, aryl, or benzyl, or $R^1$ is hydrogen, alkyl, alkenyl, or an alkoxy substituted with butyl, alkenyl, haloalkyl, aryl, or benzyl.

A fourth embodiment includes the compound according to the compound according to any one of the first to the third embodiments, wherein $R^1$ is alkoxy optionally substituted with alkyl, alkenyl, haloalkyl, aryl, or benzyl.

A fifth embodiment includes the compound according to the compound according to any one of the first to the fourth embodiments, wherein the compound is any one of the compounds disclosed in FIG. 11, FIG. 12, and/or Tables 2-5.

A sixth embodiment includes the compound according to any one of the first to the fifth embodiments, wherein the compound comprises at least one compound comprising

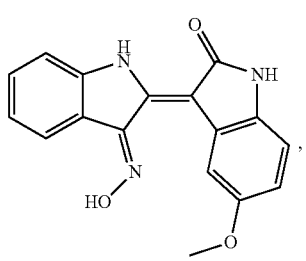

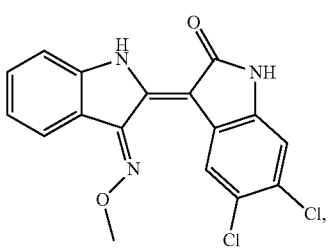

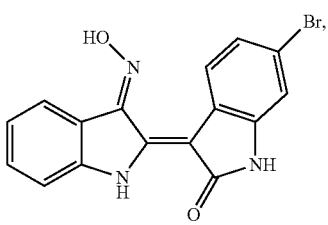

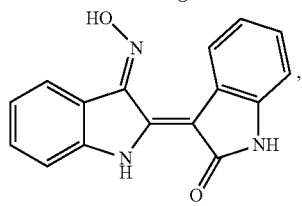

-continued

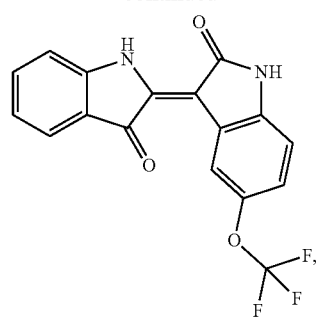

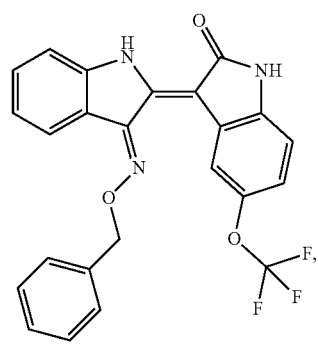

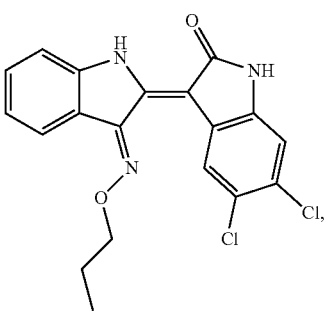

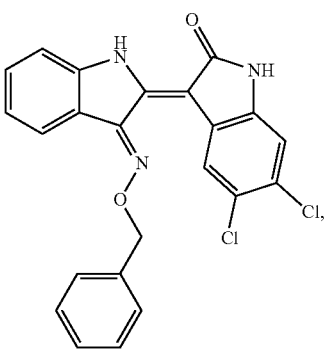

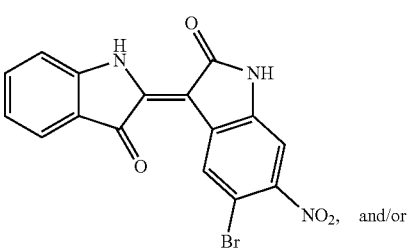

-continued

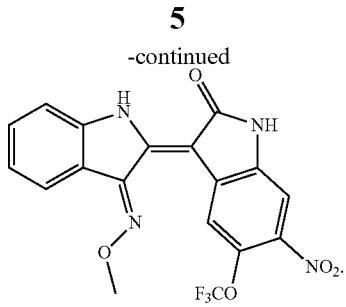

A seventh embodiment includes a compound of Formula II for use in a method of treating a condition and/or disease associated with neurodegenerative diseases or a related clinical condition in a subject,

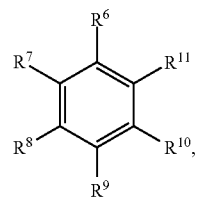
II wherein $R^6$, $R^7$, $R^8$, $R^9$, and $R^{10}$ are independently hydrogen, halogen, hydroxy, alkyl, haloalkyl, alkoxy, or

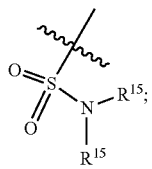

$R^{11}$ is $C_1$-$C_6$ alkyl, $C_1$-$C_6$ alkenyl, N, diimide, each substituted with $R^{12}$,

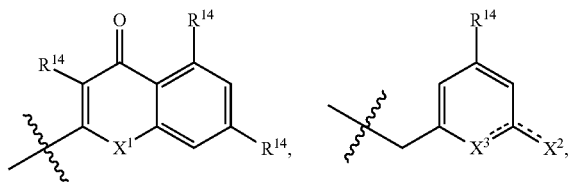

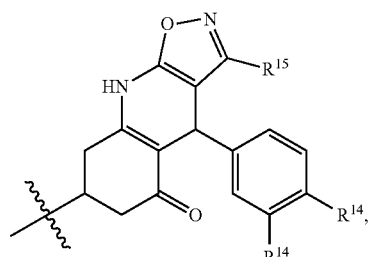

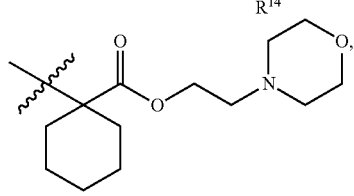

-continued

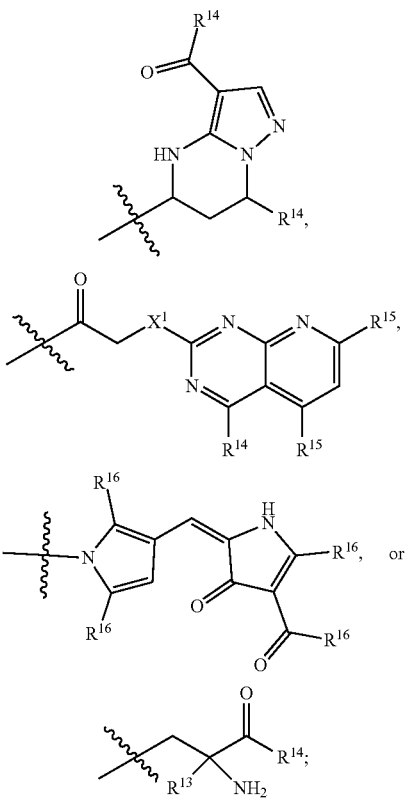

or
$R^{11}$ is

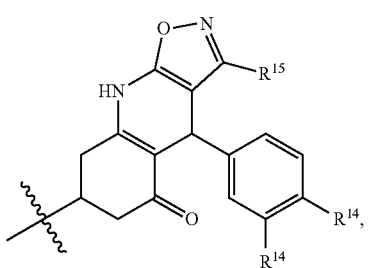

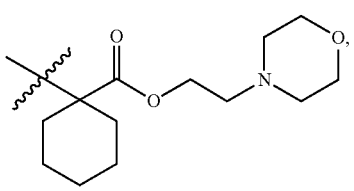

-continued

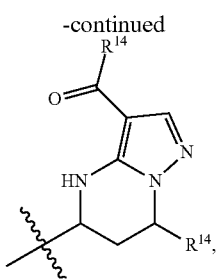

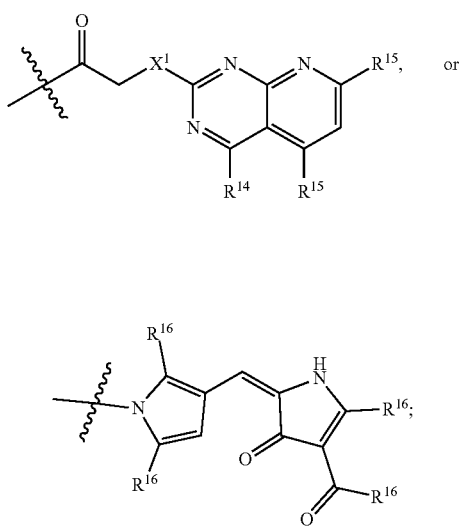

R[12] is

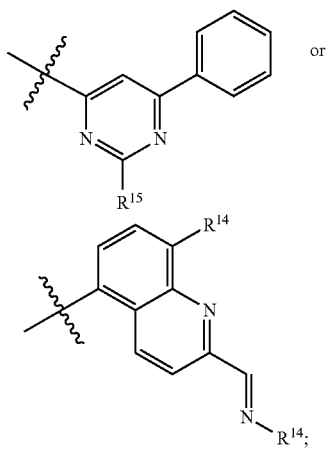

R[13] is hydrogen or an alkyl optionally substituted with hydrogen, halogen, hydroxy, alkoxy, or haloalkyl;

each R[14], each R[15], and each R[16] are independently hydrogen; halogen; haloalkyl optionally substituted with hydrogen, halogen, hydroxy, or alkoxy; alkyl optionally substituted with hydrogen, halogen, hydroxy, or haloalkyl; alkoxy optionally substituted with hydrogen, halogen, hydroxy, alkoxy, or haloalkyl; alkenyl optionally substituted with hydrogen, halogen, hydroxy, alkoxy, or haloalkyl; or alkynyl optionally substituted with hydrogen, halogen, hydroxy, alkoxy, or haloalkyl; and X[1], X[2] and X[3] are independently carbon, nitrogen, oxygen, or sulfur.

An eighth embodiment includes the compound according to the seventh embodiment, wherein R[11] is N or diimide, each substituted with R[12].

A ninth embodiment includes the compound according to any one of the seventh to the eighth embodiments, wherein R[11] is

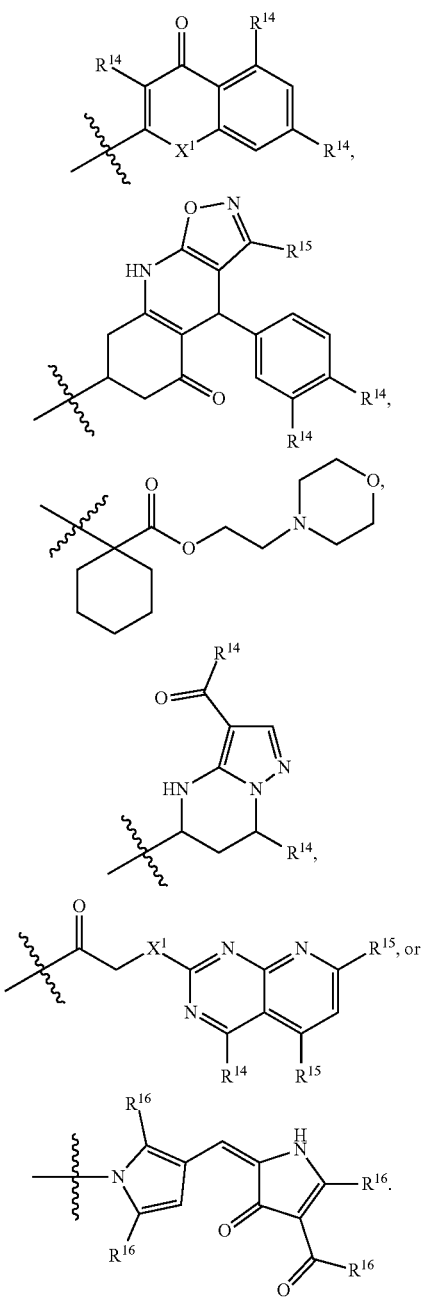

A tenth embodiment includes the compound according to any one of the seventh to the ninth embodiments, wherein the compound is

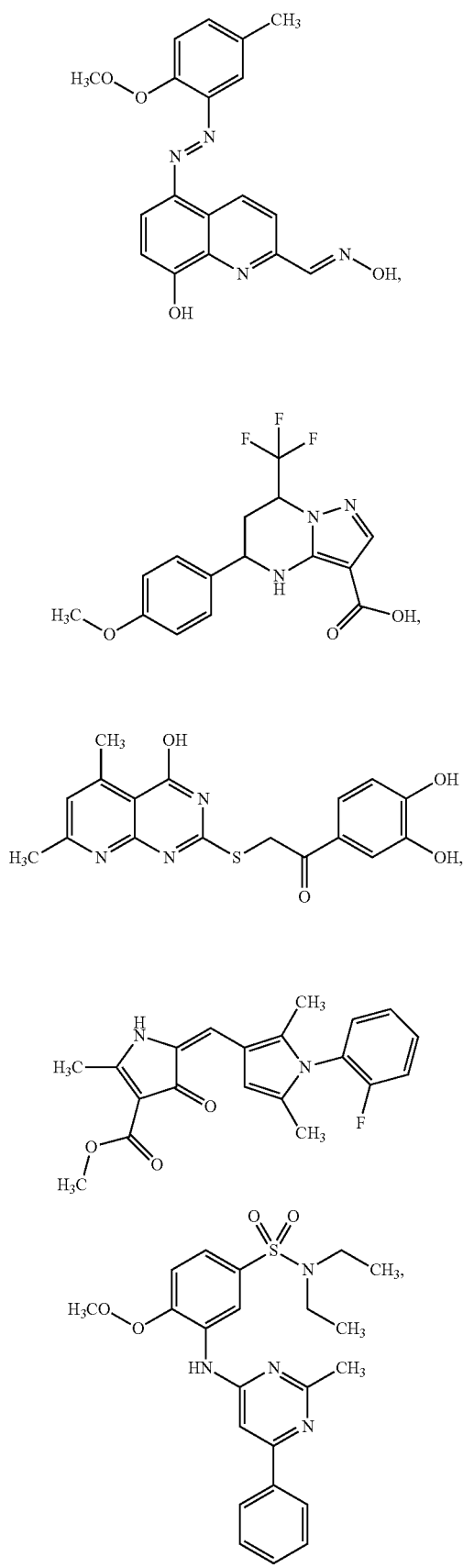
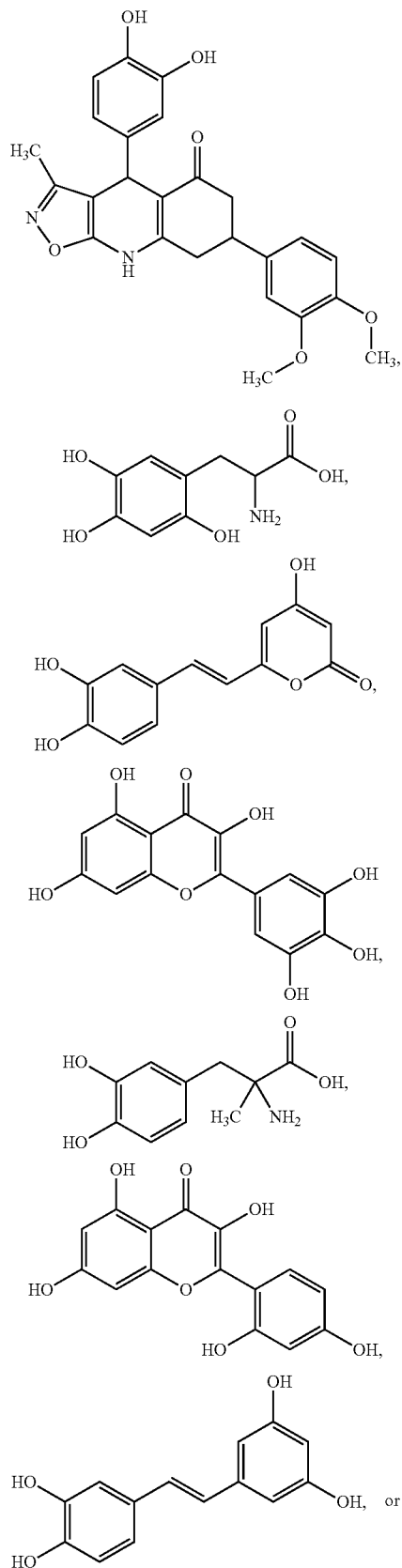

-continued

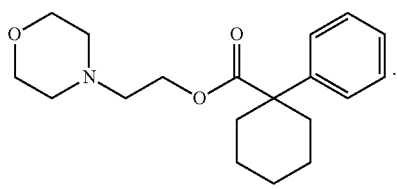

An eleventh embodiment includes a compound of Formula III for use in a method of treating a condition and/or disease associated with neurodegenerative diseases or a related clinical condition in a subject,

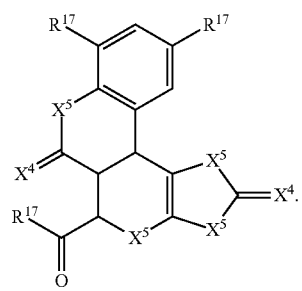

wherein each $R^{17}$ is independently hydrogen; halogen; haloalkyl optionally substituted with hydrogen, halogen, hydroxy, or alkoxy; alkyl optionally substituted with hydrogen, halogen, hydroxy, alkoxy, or haloalkyl; alkoxy optionally substituted with hydrogen, halogen, hydroxy, alkoxy, or haloalkyl; alkenyl optionally substituted with hydrogen, halogen, hydroxy, alkoxy, or haloalkyl; or alkynyl optionally substituted with hydrogen, halogen, hydroxy, alkoxy, or haloalkyl;

$X^4$ and $X^5$ are independently nitrogen, oxygen, or sulfur.

A twelfth embodiment includes the compound according to the eleventh embodiment, wherein each $R^{17}$ is independently halogen or hydroxy.

A thirteenth embodiment includes the compound according to any one of the eleventh to the twelfth embodiments, wherein the compound is

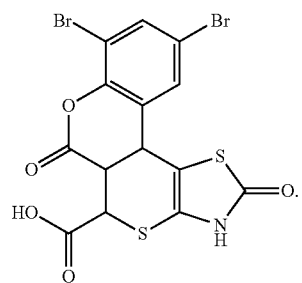 [SMILES: O=C(O)C1Sc2[nH]c(=O)sc2C2c3cc(Br)cc(Br)c3OC(=O)C12]

A fourteenth embodiment includes a compound of Formula IV for use in a method of treating a condition and/or disease associated with neurodegenerative diseases or a related clinical condition in a subject,

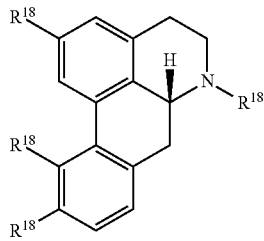

wherein each $R^{18}$ and $R^{19}$ are independently hydrogen; hydroxy; halogen; haloalkyl optionally substituted with hydrogen, halogen, hydroxy, or alkoxy; alkyl optionally substituted with hydrogen, halogen, hydroxy, alkoxy, or haloalkyl; alkoxy optionally substituted with hydrogen, halogen, hydroxy, alkoxy, or haloalkyl; alkenyl optionally substituted with hydrogen, halogen, hydroxy, alkoxy, or haloalkyl; or alkynyl optionally substituted with hydrogen, halogen, hydroxy, alkoxy, or haloalkyl.

A fifteenth embodiment includes the compound according to the fourteenth embodiments, wherein $R^{19}$ is alkyl optionally substituted with hydrogen, halogen, hydroxy, alkoxy, or haloalkyl.

A sixteenth embodiment includes the compound according to any one of fourteenth to the fifteenth embodiments, wherein each $R^{18}$ is independently hydrogen, hydroxy, halogen, alkoxy, alkyl, alkenyl, or haloalkyl.

A seventeenth embodiment includes the compound according to any one of fourteenth to the sixteenth embodiment, wherein the compound is

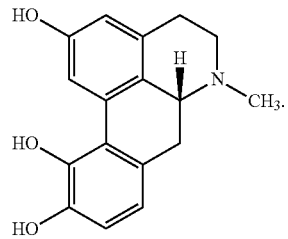

An eighteenth embodiment includes a compound of Formula V for use in a method of treating a condition and/or disease associated with neurodegenerative diseases or a related clinical condition in a subject,

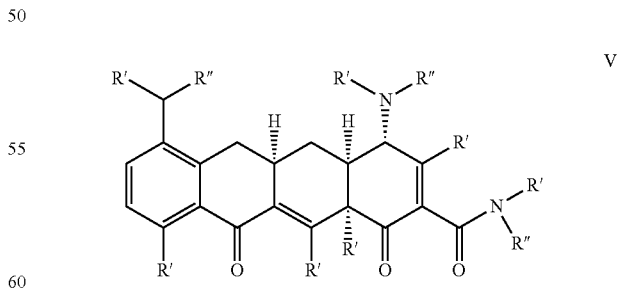

wherein each R' and each R" are independently hydrogen; halogen; haloalkyl optionally substituted with hydrogen, halogen, hydroxy, or alkoxy; alkyl optionally substituted with hydrogen, halogen, hydroxy, alkoxy, or haloalkyl; alkoxy optionally substituted with hydrogen, halogen, hydroxy, alkoxy, or haloalkyl; alkenyl optionally substituted with hydrogen, halogen, hydroxy, alkoxy, or haloalkyl; or alkynyl optionally substituted with hydrogen, halogen, hydroxy, alkoxy, or haloalkyl.

A nineteenth embodiment includes the compound according to the eighteenth embodiment, wherein each R' and each R" are independently hydrogen, halogen, hydroxy, alkyl, alkenyl, alkoxy, or haloalkyl.

A twentieth embodiment includes the compound according to any one of the eighteenth to the nineteenth embodiments, wherein the compound is

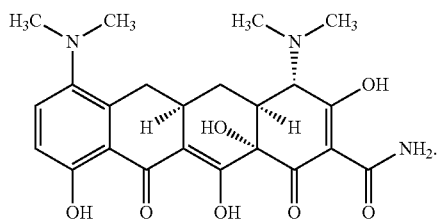

A twenty first embodiment includes a compound of Formula VI for use in a method of treating a condition and/or disease associated with neurodegenerative diseases or a related clinical condition in a subject,

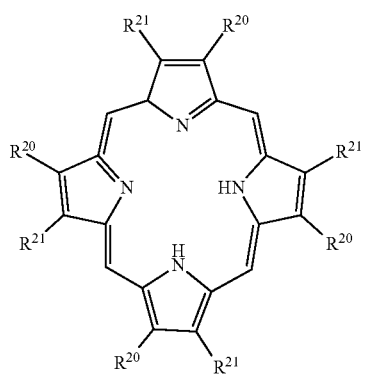

wherein each $R^{20}$ and each $R^{21}$ are independently hydrogen; halogen; haloalkyl optionally substituted with hydrogen, halogen, hydroxy, or alkoxy; alkyl optionally substituted with hydrogen, halogen, hydroxy, alkoxy, haloalkyl, or a carbonyl, optionally substituted with hydrogen, halogen, alkyl, hydroxy, alkoxy, or haloalkyl; alkoxy optionally substituted with hydrogen, halogen, hydroxy, alkoxy, or haloalkyl; alkenyl optionally substituted with hydrogen, halogen, hydroxy, alkoxy, or haloalkyl; or alkynyl optionally substituted with hydrogen, halogen, hydroxy, alkoxy, or haloalkyl.

A twenty second embodiment includes the compound according to the twenty first embodiment, wherein each $R^{20}$ and each $R^{21}$ are independently hydrogen, halogen, hydroxy, alkyl, alkenyl, alkoxy, carbonyl, carboxyl, or haloalkyl.

A twenty third embodiment includes the compound according to any one of the twenty first to the twenty second embodiments, wherein the compound is

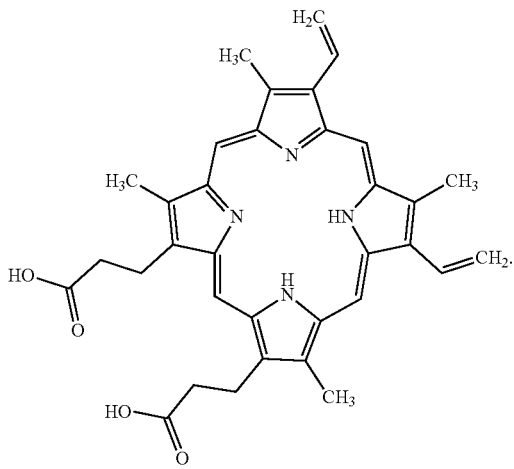 [SMILES: C=CC1=C(C)c2cc3nc(cc4[nH]c(cc5[nH]c(cc1n2)c(C)c5C=C)c(C)c4CCC(=O)O)C(CCC(=O)O)=C3C]

A twenty fourth embodiment includes at least one of the compounds according to any one of the first to the twenty third embodiments, wherein the compound inhibits or reduces the CXXC5-DVL interface, the interaction between CXXC5 and DVL, and/or the activity of CXXC5 and/or the CXXC5-DVL interface; and/or wherein the compound increases or enhances the expression and/or activity of GLP-1 in a subject; and/or wherein the neurodegenerative disease or a similar condition includes at least one condition selected from, or comprising, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

A twenty fifth embodiment includes at least one of the compounds according to any one of the preceding embodiments, wherein the compound inhibits or reduces the interaction between CXXC5 and DVL by directly competing with CXXC5 for a binding site in DVL, by directly binding to DVL, and/or by directly binding to the PZD domain of DVL.

A twenty sixth embodiment includes a pharmaceutical composition comprising at least one compound according to any one of the first to the twenty fifth embodiments and/or a pharmaceutically acceptable hydrate, salt, metabolite, or carrier thereof.

In a second aspect, methods disclosed herein include methods of treating at least one clinical condition, comprising administering to a subject at least one therapeutically effective dose of any of the compositions disclosed herein. The subject can be diagnosed with a clinical condition selected from and/or comprising neurodegenerative diseases such as Alzheimer's disease and Parkinson's disease or a similar condition thereof. In certain embodiments, the methods disclosed herein further comprise administering to the subject at plurality of therapeutically effective doses of any of the compositions disclosed herein.

A twenty seventh embodiment includes a method of treating a neurodegenerative disease or a similar condition, comprising: administering to a subject at least one therapeutically effective dose of at least one agent that inhibits or reduces the CXXC5-DVL interface the interaction between CXXC5 and DVL, and/or the activity of the CXXC5 and/or the CXXC5-DVL interface; and/or administering to a subject at least one therapeutically effective dose of at least one agent that enhances the expression and/or activity of GLP-1; and/or administering to a subject at least one therapeutically effective dose of at least one agent comprising at least one compound according to any one of the first to the twenty fifth embodiments and/or at least one composition according to the twenty sixth embodiment.

A twenty eighth embodiment includes the method according to the twenty seventh embodiment, further comprising: detecting an upregulated expression of CXXC5 in the subject. Consistent with these embodiments, the upregulated expression of CXXC5 can be detected in the blood, blood mononuclear cells, central nervous system, and/or brain of the subject.

A twenty ninth embodiment includes the method according to any one of the twenty seventh to the twenty eighth embodiments, further comprising: identifying the subject at risk for a neurodegenerative disease or a similar condition.

A thirtieth embodiment includes at least one of the methods according to any one of the twenty seventh to the twenty ninth embodiments, wherein the neurodegenerative disease or a similar condition includes at least one condition selected from, or comprising, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

A thirty first embodiment includes at least one of the methods according to any one of the twenty seventh to the thirtieth embodiments, wherein the subject exhibits abnormal GLP-1 levels, lipid profile, insulin resistance, and/or blood glucose levels.

A thirty second embodiment includes at least one of the methods according to any one of the twenty seventh to the thirty first embodiments, wherein the subject is diagnosed with obesity, diabetes, non-alcoholic fatty liver disease (NAFLD), non-alcoholic steatohepatitis (NASH), dementia, Alzheimer's disease (AD), and/or Parkinson's disease (PD).

A thirty third embodiment includes at least one of the methods according to any one of the twenty seventh to the thirty second embodiments, wherein the at least one agent that inhibits the CXXC5-DVL interface, that inhibits the interaction between CXXC5 and DVL, that inhibits the activity of CXXC5 and/or the CXXC5-DVL interface, and/or that enhances the expression and/or activity of GLP-1 comprises at least one compound according to any one of the first to the twenty fifth embodiments and/or at least one composition according to the twenty sixth embodiment.

A thirty fourth embodiment includes at least one of the methods according to the thirty third embodiments, wherein the method further includes: administering at least one therapeutically effective dose of at least one additional agent selected from, or comprising, a GSK3β inhibitor, an inhibitor of Wnt/β-catenin pathway, GLP-1 analogues, GLP-1 receptor agonists, a weight-loss medication, and/or a diabetes medication. Consistent with these embodiments, the at least one additional agent comprises orlistat, lorcaserin, phentermine-topiramate, naltrexone-bupropion, liraglutide, benzphetamine, diethylpropion, sulfonylureas, meglitinides, thiazolidinediones, DPP-4 inhibitors, insulin analog, alpha glucosidase inhibitor, SGL T2 inhibitors, sitagliptin, metformin, rosiglitazone, ocaliva, selonsertib, elafibranol, ceniciriviroc, MGL-3196, GR-MD-02, aramchol, GLP-1 analogues, and/or GLP-1 receptor agonists.

A thirty fifth embodiment includes at least one of the methods according to any one of the twenty seventh to the thirty fourth embodiments, wherein the subject is a human adult, a human child, and/or an animal.

A thirty sixth embodiment includes at least one of the methods according to any one of the twenty seventh to the thirty fifth embodiments, wherein the at least one agent and/or the at least one additional agent is administered orally, nasally, subcutaneously, or intravenously.

A thirty seventh embodiment includes at least one of the methods according to any one of the twenty seventh to the thirty sixth embodiments, wherein the therapeutically effective dose of at least one compound according to any one of the first to the twenty fifth embodiments and/or at least one composition according to the twenty sixth embodiment, is on the order of between about 5 mg to about 2000 mg and the dose of the compound is administered to the subject at least once per day. In some embodiments, the therapeutically effective dose of at least one compound according to any one of the first to the twenty fifth embodiments and/or at least one composition according to the twenty sixth embodiment, includes, but is not limited to, on the order of between: about 10 mg to about 1900 mg; about 15 mg to about 1800 mg; about 15 mg to about 1700 mg; about 20 mg to about 1600 mg; about 25 mg to about 1500 mg; about 30 mg to about 1000 mg; about 50 mg to about 1000 mg; about 50 mg to about 800 mg; about 100 mg to about 800 mg; about 300 mg to about 800 mg; about 500 mg to about 800 mg; about 5 mg to about 50 mg; about 1000 mg to about 1700 mg; about 1200 mg to about 1700 mg; about 1500 mg to about 1700 mg; about 10 mg to about 1000 mg; about 10 mg to about 30 mg; about 1500 mg to about 2000 mg; about 100 mg to about 200 mg; about 100 mg to about 150 mg; and/or any combination thereof. Consistent with these embodiments, the therapeutically effective dose of at least one compound according to any one of the first to the twenty fifth embodiments and/or at least one composition according to the twenty sixth embodiment, includes, but not limited to, on the order of between: about 1 mg/m2 to about 1500 mg/m2; about 10 mg/m2 to about 1000 mg/m2; about 20 mg/m2 to about 800 mg/m2; about 10 mg/m2 to about 50 mg/m2; about 800 mg/m2 to about 1200 mg/m2; about 50 mg/m2 to about 500 mg/m2; about 500 mg/m2 to about 1000 mg/m2; about 80 mg/m2 to about 150 mg/m2; about 80 mg/m2 to about 120 mg/m2; and/or any combination thereof.

A thirty eighth embodiment includes at least one of the methods according to any one of the twenty seventh to the thirty sixth embodiments, wherein the therapeutically effective dose of at least one compound according to any one of the first to the twenty fifth embodiments and/or at least one composition according to the twenty sixth embodiment, is on the order of between about 0.01 mg to about 200 mg and the dose of the compound is administered to the subject at least once per day. In some embodiments, the therapeutically effective dose of at least one compound according to any one of the first to the twenty fifth embodiments and/or at least one composition according to the twenty sixth embodiment, includes, but is not limited to, on the order of between: about 0.01 mg to about 150 mg; about 0.01 mg to about 100 mg;

about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. In some of these embodiments, the therapeutically effective dose of at least one compound according to any one of the first to the twenty fifth embodiments and/or at least one composition according to the twenty sixth embodiment, includes, but not limited to, on the order of between: about 0.01 mg/m$^2$ to about 100 mg/m$^2$; about 0.01 mg/m$^2$ to about 80 mg/m$^2$; about 0.01 mg/m$^2$ to about 50 mg/m$^2$; about 0.01 mg/m$^2$ to about 25 mg/m$^2$; about 0.05 mg/m$^2$ to about 100 mg/m$^2$; about 0.05 mg/m$^2$ to about 80 mg/m$^2$; about 0.05 mg/m$^2$ to about 50 mg/m$^2$; about 80 mg/m$^2$ to about 150 mg/m$^2$; about 80 mg/m$^2$ to about 120 mg/m$^2$; and/or any combination thereof.

In a third aspect, methods provided by the present application reduce and/or suppress a side effect of a therapeutic regime, the methods comprising administering to a subject at least one therapeutically effective dose of at least one agent that inhibits or reduces the CXXC5-DVL interface in a subject and/or that enhances the expression and/or activity of GLP-1, and/or administering to a subject at least one therapeutically effective dose of at least one agent comprising at least one compound according to any one of the first to the twenty fifth embodiments and/or at least one composition according to the twenty sixth embodiment; wherein the subject has received at least one therapeutic regime selected from drug therapy, surgical treatment, and/or combinations thereof, and wherein the subject experiences at least one side effect as a consequence of the therapeutic regime. Consistent with these embodiments, side effects can include, but are not limited to, drug-resistance, relapse, inflammation, or any combination thereof.

A thirty ninth embodiment includes a method of detecting one or more neurodegenerative markers, comprising: providing a sample of blood, cells, or tissues from a subject suspected of having or known to have a metabolic and/or neurodegenerative disease or condition; and detecting upregulation in CXXC5 and/or β-catenin in the sample, and/or detecting downregulation of GLP-1.

A fortieth embodiment includes the method according to the thirty ninth embodiment, wherein the neurodegenerative disease or a similar condition includes at least one condition selected from, or comprising, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

Consistent with all of preceding embodiments, wherein CXXC5 is overexpressed in the blood, brain and/or central nervous system of the subject at least about 10%, about 20%, about 25%, about 30%, about 40%, about 50%, about 60%, about 70%, about 80%, about 90%, about 100%, about 200%, about 300%, about 400%, about 500%, and/or about 1000%, or any combination thereof, as compared to that of a normal subject known not to have a metabolic and/or neurodegenerative disease; and/or CXXC5 is overexpressed in the blood, brain and/or central nervous system of the subject at least about 1.5 fold, about 2 fold, about 2.5 fold, about 3 fold, about 3.5 fold, about 4 fold, about 4.5 fold, about 5 fold, about 6 fold, about 7 fold, about 8 fold, about 9 fold, about 10 fold, about 15 fold, about 20 fold, about 25 fold, about 50 fold, and/or about 100 fold, or any combination thereof, as compared to that of a normal subject known not to have a metabolic and/or neurodegenerative disease.

A forty first embodiment includes at least one of the methods according to the thirty ninth to the fortieth embodiments, further comprising: treating the subject using at least one method according to any one of the twenty seventh to the thirty eighth embodiments.

A forty second embodiment includes a method of enhancing the activity of GLP-1 in a subject, comprising the steps of: providing a subject at least one therapeutically effective dose of at least one compound according to any the first to the twenty fifth embodiments, or a pharmaceutically acceptable salt thereof, or a metabolite thereof; and/or wherein the effective dose of the at least one compound enhances the activity of GLP-1 and/or the expression of GLP-1.

A forty third embodiment includes the method according to the forty second embodiment, wherein the subject comprises a human, an animal, a cell, and/or a tissue.

A forty fourth embodiment includes a method of reducing resistance to a therapeutic regime, comprising: administering to a subject at least one therapeutically effective dose of at least one agent that inhibits or reduces the CXXC5-DVL interface the interaction between CXXC5 and DVL, and/or the activity of the CXXC5 and/or the CXXC5-DVL interface; and/or administering to a subject at least one therapeutically effective dose of at least one agent comprising at least one compound according to any one of the first to the twenty fifth embodiments and/or at least one composition according to the twenty sixth embodiment.

A forty fifth embodiment includes the method according to the forty fourth embodiment, wherein wherein the at least one agent that inhibits the CXXC5-DVL interface, that inhibits the interaction between CXXC5 and DVL, and/or that inhibits the activity of CXXC5 and/or the CXXC5-DVL interface comprises at least one compound according to any one of the first to the twenty fifth embodiments and/or at least one composition according to the twenty sixth embodiment.

A forty sixth embodiment includes the method according to any one of the forty fourth to the forty fifth embodiments, wherein the subject was previously or is being concomitantly treated with at least one therapeutic regime including, but is not limited to, surgery, weight loss, healthy eating, physical activity, insulin therapy, and/or a medication/drug therapy; and/or wherein the subject is diagnosed with a disease or having a condition contributed to neurodegenerative diseases, due at least in part by the suppressed expression of active GLP-1 in a subject.

A forty seventh embodiment includes the method according to any one of the forty fourth to the forty sixth embodiments, wherein the subject was previously or is being concomitantly treated with at least one medication including, but is not limited to, orlistat, lorcaserin, phentermine-topiramate, naltrexone-bupropion, liraglutide, benzphetamine, diethylpropion, sulfonylureas, meglitinides, thiazolidinediones, dipeptidylpeptidase-4 (DPP-4) inhibitors, insulin analog, alpha glucosidase inhibitor, SGL T2 inhibitors, sitagliptin, metformin, rosiglitazone, ocaliva, selonsertib, elafibranol, cenicriviroc, MGL-3196, GR-MD-02, aramchol, GLP-1 analogues, and/or GLP-1 receptor agonist.

A forty eighth embodiment includes a kit for for carrying out any one of the preceding methods disclosed herein. Components of the kit include, but are not limited to, one or more of agents/compositions disclosed herein, reagents, containers, equipment and/or instructions for using the kit.

A forty ninth embodiment includes the kit according to the forty eighth embodiment, wherein the one or more of agents/compositions includes at least one compound according to any one of the first to the twenty fifth embodiments and/or at least one composition according to the twenty sixth embodiment.

A fiftieth embodiment includes at least one of the methods according to any one of the twenty seventh to the forty seventh embodiments, wherein the therapeutically effective dose of at least one compound according to any one of the first to the twenty fifth embodiments and/or at least one composition according to the twenty sixth embodiment, is on the order of between about 5 mg to about 2000 mg and the dose of the compound is administered to the subject at least once per day. In some embodiments, the therapeutically effective dose of at least one compound according to any one of the first to the twenty fifth embodiments and/or at least one composition according to the twenty sixth embodiment, includes, but is not limited to, on the order of between: about 10 mg to about 1900 mg; about 15 mg to about 1800 mg; about 15 mg to about 1700 mg; about 20 mg to about 1600 mg; about 25 mg to about 1500 mg; about 30 mg to about 1000 mg; about 50 mg to about 1000 mg; about 50 mg to about 800 mg; about 100 mg to about 800 mg; about 300 mg to about 800 mg; about 500 mg to about 800 mg; about 5 mg to about 50 mg; about 1000 mg to about 1700 mg; about 1200 mg to about 1700 mg; about 1500 mg to about 1700 mg; about 10 mg to about 1000 mg; about 10 mg to about 30 mg; about 1500 mg to about 2000 mg; about 100 mg to about 200 mg; about 100 mg to about 150 mg; and/or any combination thereof. Consistent with these embodiments, the therapeutically effective dose of at least one compound according to any one of the first to the twenty fifth embodiments and/or at least one composition according to the twenty sixth embodiment, includes, but not limited to, on the order of between: about 1 mg/m2 to about 1500 mg/m2; about 10 mg/m2 to about 1000 mg/m2; about 20 mg/m2 to about 800 mg/m2; about 10 mg/m2 to about 50 mg/m2; about 800 mg/m2 to about 1200 mg/m2; about 50 mg/m2 to about 500 mg/m2; about 500 mg/m2 to about 1000 mg/m2; about 80 mg/m2 to about 150 mg/m2; about 80 mg/m2 to about 120 mg/m2; and/or any combination thereof.

A fifty first embodiment includes at least one of the methods according to any one of the twenty seventh to the forty seventh embodiments, wherein the therapeutically effective dose of at least one compound according to any one of the first to the twenty fifth embodiments and/or at least one composition according to the twenty sixth embodiment, is on the order of between about 0.01 mg to about 200 mg and the dose of the compound is administered to the subject at least once per day. In some embodiments, the therapeutically effective dose of at least one compound according to any one of the first to the twenty fifth embodiments and/or at least one composition according to the twenty sixth embodiment, includes, but is not limited to, on the order of between: about 0.01 mg to about 150 mg; about 0.01 mg to about 100 mg; about 0.01 mg to about 80 mg; about 0.01 mg to about 60 mg; about 0.05 mg to about 100 mg; about 0.05 mg to about 80 mg; about 0.05 mg to about 50 mg; about 0.1 mg to about 100 mg; about 0.1 mg to about 50 mg; about 0.2 mg to about 100 mg; about 0.2 mg to about 50 mg; about 0.5 mg to about 100 mg; about 0.5 mg to about 50 mg; about 100 mg to about 200 mg; about 100 mg to about 150 mg; and/or any combination thereof. In some of these embodiments, the therapeutically effective dose of at least one compound according to any one of the first to the twenty fifth embodiments and/or at least one composition according to the twenty sixth embodiment, includes, but not limited to, on the order of between: about 0.01 mg/m$^2$ to about 100 mg/m$^2$; about 0.01 mg/m$^2$ to about 80 mg/m$^2$; about 0.01 mg/m$^2$ to about 50 mg/m$^2$; about 0.01 mg/m$^2$ to about 25 mg/m$^2$; about 0.05 mg/m$^2$ to about 100 mg/m$^2$; about 0.05 mg/m$^2$ to about 80 mg/m$^2$; about 0.05 mg/m$^2$ to about 50 mg/m$^2$; about 80 mg/m$^2$ to about 150 mg/m$^2$; about 80 mg/m$^2$ to about 120 mg/m$^2$; and/or any combination thereof.

A fifty second embodiment includes a method of determining the presence of a neurodegenerative disease in a subject, the method comprising assaying for a level of expression of CXXC5 gene and/or a level of expression of CXXC5 protein that is elevated in the blood, brain and/or central nervous system of a subject as compared to a reference value.

A fifty third embodiment includes the method according to the fifty second embodiment, wherein the neurodegenerative disease includes at least one condition selected from, or comprising, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

A fifty fourth embodiment includes the method according to any one of the fifty second to the fifty third embodiments, wherein the reference value is the level of expression of CXXC5 gene or the level of expression of CXXC5 protein in a normal subject known not to have a metabolic and/or neurodegenerative disease.

A fifty fifth embodiment includes the method according to any one of the fifty second to the fifty fourth embodiments, further assaying for a level of expression of GLP-1 gene and/or a level of expression of GLP-1 protein that is reduced in the blood, brain, blood, brain and/or central nervous system, white adipose tissue, pancreas, and/or intestine of a subject as compared to a reference value.

A fifty sixth embodiment includes the method according to any one of the fifty second to the fifty fifth embodiments, wherein the level of expression of CXXC5 gene and/or the level of expression of CXXC5 protein is elevated at least about 10%, about 20%, about 25%, about 30%, about 40%, about 50%, about 60%, about 70%, about 80%, about 90%, about 100%, about 200%, about 300%, about 400%, about 500%, and/or about 1000%, or any combination thereof, as compared to the reference value; and/or wherein the level of expression of CXXC5 gene and/or the level of expression of CXXC5 protein is elevated at least about 1.5 fold, about 2 fold, about 2.5 fold, about 3 fold, about 3.5 fold, about 4 fold, about 4.5 fold, about 5 fold, about 6 fold, about 7 fold, about 8 fold, about 9 fold, about 10 fold, about 15 fold, about 20 fold, about 25 fold, about 50 fold, and/or about 100 fold, or any combination thereof, as compared to the reference value.

A fifty seventh embodiment includes at least one of the methods according to the any one of the fifty second to the fifty sixth embodiments, further comprising: contacting CXXC5 with at least one agent comprising at least one compound according to any one of the first to the twenty fifth embodiments and/or at least one composition according to the twenty sixth embodiment.

A fifty eighth embodiment includes at least one of the methods according to the any one of the fifty second to the fifty seventh embodiments, further comprising: detecting the presence of CXXC5 in the brain and/or central nervous system of the subject.

A fifty ninth embodiment includes at least one of the methods according to the any one of the fifty second to the fifty eighth embodiments, further comprising: treating the subject using at least one method according to any one of the twenty seventh to the thirty eighth embodiments and the fiftieth to the fifty first embodiments.

A sixtieth embodiment includes at least one of the methods according to any one of the fifty second to the fifty ninth embodiments, wherein the subject comprises a cell, an animal, or a human. Consistent with these embodiments, the cell can include adipocytes, blood mononuclear cells, and/or neurons.

A sixty first embodiment includes use of a composition comprising at least one compound according to any one of the first to the twenty fifth embodiments or a pharmaceutically acceptable hydrate, salt, metabolite, or carrier thereof in the manufacture of a medicament for neurodegenerative diseases or a related clinical condition.

A sixty second embodiment includes the method or the use of any preceding embodiments, wherein the composition is administered to the subject orally, topically, nasally, parenterally, paracancerally, transmucosally, transdermally, intramuscularly, intravenously, intradermally, subcutaneously, intraperitoneally, intraventricularly, intracranially, intratumorally, or by pulmonary delivery.

A sixty third embodiment includes the use of the sixty first to the sixty second embodiments, wherein the neurodegenerative diseases or a related clinical condition includes at least one condition selected from, or comprising, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

DEFINITIONS

Figure 1A:
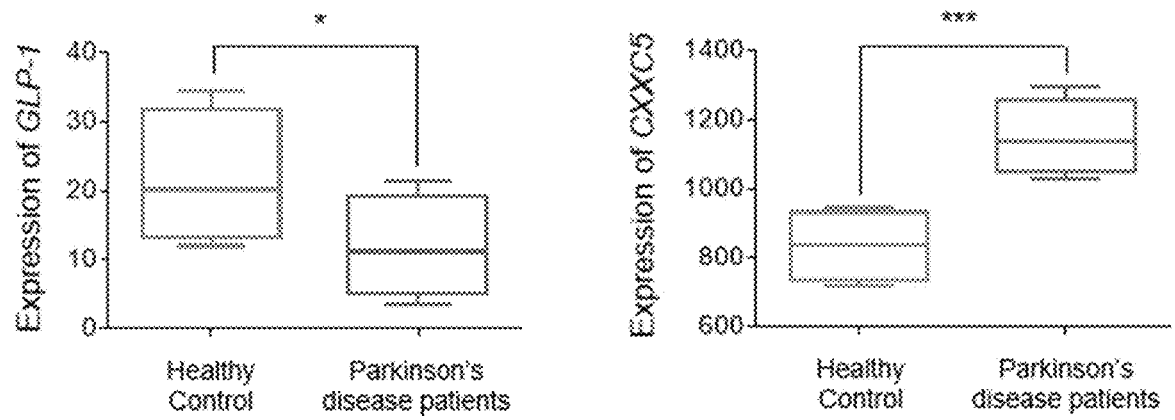
FIG. 1A. Graphs illustrating the mRNA expression levels of GLP-1 and CXXC5 in the peripheral blood of untreated patients with stage 1 Parkinson's disease (PD) compared to the normal healthy control (mean±s.e.m., n=4, *P<0.05 and ***P<0.0005).

"About" refers to a range of values plus or minus 10 percent, e.g. about 1.0 encompasses values from 0.9 to 1.1.

"CXXC5-DVL interface" refers to an interaction and/or association between CXXC5 (CXXC finger protein 5) and DVL (disheveled), which can induce biological activities known in the art. The interactions and/or associations can be physical or chemical interactions that would activate a CXXC5-DVL pathway within a subject. CXXC5-DVL interface can be present in a form of a complex.

"Inhibitor of CXXC5-DVL interface" refers to an agent that alters the function and/or activity of the CXXC5-DVL interface or induces conformational changes in the CXXC5-DVL interface. Examples of inhibitors of CXXC5-DVL interface include, but are not limited to, agents that alter association/dissociation between CXXC5 and DVL and/or agents that inhibit CXXC5-DVL complex assembly/function.

"Neurodegenerative disease or a similar condition" can include, but is not limited to, dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

"Metabolic disease or a similar condition" can include, but is not limited to, metabolic disorder, metabolic syndrome, obesity, high blood pressure, high blood sugar, high serum triglycerides, hyperuricemia, fatty liver, polycystic ovarian syndrome, erectile dysfunction, acanthosis *nigricans*, type 2 diabetes mellitus, hypoadiponectinemia, cirrhosis, portal hypertension, cardiovascular diseases, coronary artery disease, lipodystrophy, dyslipidemia, hepatic steatosis, non-alcoholic fatty liver disease (NAFLD), and/or non-alcoholic steatohepatitis (NASH).

"Pharmaceutically acceptable" refers to approved or approvable by a regulatory agency of a government, such as the U.S. FDA or the EMA, or listed in the U.S. Pharmacopoeia or other generally recognized pharmacopoeia for use in mammals and/or animals, and more particularly in humans.

"Pharmaceutically acceptable vehicle" or "pharmaceutically acceptable carrier," unless stated or implied otherwise, is used herein to describe any ingredient other than the active component(s) that can be included in a formulation. The choice of carrier will to a large extent depend on factors such as the mode of administration, the effect of the carrier on solubility and stability, and the nature of the dosage form.

"Pharmaceutical composition" refers to a therapeutically active inhibitor of CXXC5-DVL interface or a therapeutically active inhibitor of GSKβ, and at least one pharmaceutically acceptable vehicle/carrier, with which the inhibitor of CXXC5-DVL interface and/or inhibitor of GSKβ is administered to a subject.

"Subject" refers to a human (adult and/or child), an animal, a livestock, a cell, and/or a tissue.

"Therapeutically effective amount" refers to the amount of an inhibitor of CXXC5-DVL interface, at least one compound disclosed herein, GLP-1 analogues, GLP-1 receptor agonist or inhibitor of GSKβ that when administered to a subject for treating a disease, or at least one of the clinical symptoms of a disease, is sufficient to affect such treatment of the disease or symptom thereof. The "therapeutically effective amount" can vary depending, for example, on the inhibitor of CXXC5-DVL interface, the disease and/or symptoms of the disease, severity of the disease and/or symptoms of the disease or disorder, the age, weight, and/or health of the subject to be treated, and the judgment of the prescribing physician.

"Therapeutically effective dose" refers to a dose that provides effective treatment of a disease or disorder in a subject. A therapeutically effective dose can vary from compound to compound, and from subject to subject, and can depend upon factors such as the condition of the subject and the route of delivery.

"Therapeutic regime(s)" and/or "therapeutic regimen(s)" include, but are not limited to, surgery, weight loss, healthy eating, physical activity, insulin therapy, and/or a medication/drug therapy. In some embodiments, the medication/drug therapy includes one or more treatments with at least one agent including, but is not limited to, orlistat, lorcaserin, phentermine-topiramate, naltrexone-bupropion, liraglutide, benzphetamine, diethylpropion, sulfonylureas, meglitinides, thiazolidinediones, DPP-4 inhibitors, insulin analog, alpha glucosidase inhibitor, SGL T2 inhibitors, sitagliptin, metformin, rosiglitazone, ocaliva, selonsertib, elafibranol, ceniCriviroc, MGL-3196, GR-MD-02, aramchol, GLP-1 analogues, and/or GLP-1 receptor agonists.

"Treat," "treating" or "treatment" of any disease or condition refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. In some embodiments, "treat," "treating" or "treatment" also refers to inhibiting the disease, either physically, (e.g., stabilization of a discernible symptom), physiologically, (e.g., stabilization of a physical parameter), or both, and to inhibiting at least one physical parameter that can or cannot be discernible to the subject. In certain embodiments, "treat," "treating" or "treatment" refers to delaying the onset of the disease or condition or at least one or more symptoms thereof in a subject which can be exposed to or predisposed to a disease or condition even though that subject does not yet experience or display symptoms of the disease.

DETAILED DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Neurodegenerative diseases possess multiplex pathological status associated with functional disorders in various systems such as motor control, cognition, perception, sensory function, and the autonomic nervous system due to the loss or decrease in neuronal function. Neurodegenerative diseases have long been considered as incurable, complex conditions that no one drug or other intervention that can treat the conditions successfully. Current approaches focus on helping people maintain mental function, manage behavioral symptoms, and slow down the symptoms of disease. Accordingly, an effective medication that improves the overall condition of neurodegenerative diseases by targeting the systemic pathological process is not currently available.

Metabolic diseases possess multiplex pathological status associated with obesity, atherogenic dyslipidemia, insulin resistance, and increased risk of developing type 2 diabetes mellitus (T2DM). Nonalcoholic steatohepatitis (NASH) can be characterized as inflammation and damage in liver caused by accumulation of fat in the liver. Many affected patients exhibit obesity, type 2 diabetes mellitus, glucose intolerance, dyslipidemia, and/or metabolic disease. Although incidences of NASH have been increasing worldwide with increase in obesity, its pathological mechanism(s) is not well understood.

Recent studies indicate Alzheimer's disease (AD) and/or Parkinson's disease (PD) possess multiplex pathological status associated with insulin resistance and type 2 diabetes mellitus (T2DM). The systemic insulin resistance accompanied by the T2DM may be associated with Parkinson's disease and patients with Parkinson's disease commonly show impaired glucose tolerance which can induce brain insulin resistance. Hyperinsulinemia and insulin resistance, which are known as pathophysiological features of the T2DM, have also been demonstrated to have significant impact on cognitive impairment. Further, the impaired insulin signaling has not only been related to α-synuclein build-up and mitochondrial dysfunction, but also behavioral abnormalities seen in Parkinson's disease patients such as impaired cognition, anxiety and depressive disorders. It is postulated that the mechanisms for cognitive impairment include impairment in cerebral insulin signaling, change in amyloid metabolism, accumulation of advanced glycation end products, and oxidative stress. In addition, some studies identified that the insulin signaling pathway may play a role in Parkinson's disease, and that there may be a link between diabetes and neurodegenerative disorders.

Alzheimer's disease, the most common form of dementia among older adults, is an irreversible degeneration of the brain that causes disruptions in memory, cognition, personality, and other functions that eventually lead to death from complete brain failure. Parkinson's disease is the most prevalent form of dementia and is characterized by cognitive insufficiencies and behavioral changes that affect memory and learning abilities, daily functioning and quality of life. Parkinson's disease may be caused by predominate loss of dopamine-producing neurons in brain.

Glucagon-like peptide-1 (GLP-1), a 30-amino acid long peptide hormone derived from the proglucagon gene and secreted from the distal small intestine when food enters the duodenum. The GLP-1 receptors are found and prevalent in the central nervous system of the brain, and when stimulated, enhance cell survival and promote neuroprotection. GLP-1 affects neurological and cognitive functions, as well as its regulatory effect on glucose metabolism. Therefore, GLP-1 receptor agonist(s) has been considered for treating neurogenerative diseases, but an effective medication that improves the overall condition of neurodegenerative diseases by targeting the systemic pathological process is not currently available.

CXXC finger protein 5 (CXXC5) is a negative regulator of Wnt/β-catenin signaling, functioning via interaction with PDZ domain of disheveled (DVL) in the cytosol. Inhibition of the CXXC5-DVL interaction improved several pathophysiological phenotypes involving Wnt/β-catenin signaling including osteoporosis, longitudinal bone growth, cutaneous wounds, and hair loss through activation of the Wnt/β-catenin signaling.

As disclosed herein, CXXC5 expression were surprisingly increased in the brain tissues of patients diagnosed with Alzheimer's disease and/or Parkinson's disease. Further, the Wnt/β-catenin signaling target gene GLP-1 was found to be suppressed by inactivation of β-catenin signaling accompanied by the CXXC5 overexpression in the brain tissues of patients having Alzheimer's disease and/or Parkinson's disease. Further, Wnt/β-catenin pathway target genes such as GLP-1, TCF7L2, and FOSL1 were found to be suppressed in patients diagnosed with AD and/or PD. $Cxxc5^{-/-}$ mice did not develop any phenotypes of neurodegenerative diseases including AD and/or PD. The results disclosed herein suggest that CXXC5 contributes to the development of neurodegenerative diseases. Thus, the instant disclosure provides a novel function of CXXC5-DVL interface that may lead to the treatment of neurodegenerative diseases including, but are not limited to, AD and/or PD.

Embodiments disclosed herein relate to compositions and methods for treating a condition and/or disease associated with neurodegenerative disease and/or a related clinical condition in a subject. In certain embodiments, compositions and methods disclosed herein concern suppression of a side effect of a therapeutic regime. Other embodiments relate to compositions and methods for treating a subject diagnosed with a neurodegenerative disease or having a condition contributed to dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS).

Methods disclosed herein include a method of treating a clinical condition, comprising administering to a subject at least one therapeutically effective dose of any one of the compounds and/or compositions disclosed herein. The subject can be diagnosed with a clinical condition selected from and/or comprising a neurodegenerative disease or a similar condition thereof. In certain embodiments, the methods disclosed herein further comprise administering to the subject at plurality of therapeutically effective doses of any one of the compounds and/or compositions disclosed herein.

In some embodiments, compositions disclosed herein comprise at least one agent that inhibits CXXC5-DVL interface in a subject. Consistent with these embodiments, the at least one agent that inhibits CXXC5-DVL interface comprises at least one compound disclosed herein. In some embodiments, the at least one agent that inhibits CXXC5-DVL interface can disrupt conformation of the CXXC5-DVL interface physically and/or chemically. Yet in some embodiments, the at least one compound disclosed herein enhances the expression and/or the activity of GLP-1 in a subject.

Pharmaceutical Compositions

Pharmaceutical compositions provided by the present disclosure can comprise a therapeutically effective amount of one or more compositions disclosed herein, together with a suitable amount of one or more pharmaceutically acceptable vehicles to provide a composition for proper administration to a subject. Suitable pharmaceutical vehicles are described in the art.

Pharmaceutical compositions of the present disclosure suitable for oral administration can be presented as discrete units, such as a capsule, cachet, tablet, or lozenge, each containing a predetermined amount of the active ingredient; as a powder or granules; as a solution or a suspension in an aqueous liquid or non-aqueous liquid such as a syrup, elixir or a draught, or as an oil-in-water liquid emulsion or a water-in-oil liquid emulsion. The composition can also be presented as a bolus, electuary, or paste. A tablet can be made by compressing or moulding the active ingredient with the pharmaceutically acceptable carrier. Compressed tablets can be prepared by compressing in a suitable machine the active ingredient in a free-flowing form, such as a powder or granules, in admixture with, for example, a binding agent, an inert diluent, a lubricating agent, a disintegrating and/or a surface-active agent. Moulded tablets can be prepared by moulding in a suitable machine a mixture of the powdered active ingredient moistened with an inert liquid diluent. The tablets can optionally be coated or scored and can be formulated to provide slow or controlled release of the active ingredient.

Pharmaceutical compositions of the present disclosure suitable for parenteral administration include aqueous and non-aqueous sterile injection solutions, and can also include an antioxidant, buffer, a bacteriostat and a solution which renders the composition isotonic with the blood of the recipient, and aqueous and non-aqueous sterile suspensions which can contain, for example, a suspending agent and a thickening agent. The formulations can be presented in a single unit-dose or multi-dose containers and can be stored in a lyophilized condition requiring the addition of a sterile liquid carrier prior to use.

Pharmaceutically acceptable salts include salts of compounds provided by the present disclosure that are safe and effective for use in mammals and that possess a desired therapeutic activity. Pharmaceutically acceptable salts include salts of acidic or basic groups present in compounds provided by the present disclosure. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain disclosed compounds may form pharmaceutically acceptable salts with various amino acids. Suitable base salts include, but are not limited to, aluminum, calcium, lithium, magnesium, potassium, sodium, zinc, and diethanolamine salts. For additional information on some pharmaceutically acceptable salts that can be used to practice the methods described herein please review articles such as Berge, et al., 66 J. PHARM. SCI. 1-19 (1977), Haynes, et al, J. Pharma. Sci., Vol. 94, No. 10, October 2005, pgs. 2111-2120, and the like.

In some embodiments, the composition can contain pharmaceutically acceptable lubricant(s). The pharmaceutically acceptable lubricant(s) prevent the components of the pharmaceutical composition from clumping together and from sticking to the pellet press that generates the disclosed compositions. The lubricant(s) also ensure that the formation of the pellet, as well as its ejection from the pellet press, occurs with low friction between the composition and the wall of the die press. In some embodiments, the lubricant(s) are added to a pharmaceutical composition to improve processing characteristics, for example to help increase the flexibility of the compositions, thereby reducing breakage.

The type of lubricant that can be used in the disclosed pharmaceutical compositions can vary. In some embodiments, the pharmaceutically acceptable lubricant is selected from talc, silica, vegetable stearin, magnesium stearate, stearic acid, calcium stearate, glyceryl behenate, glyceryl monostearate, glyceryl palmitostearate, mineral oil, polyethylene glycol, sodium stearyl fumarate, sodium lauryl sulfate, vegetable oil, zinc stearate, and combinations thereof. In some embodiments, the pharmaceutically acceptable lubricant is stearic acid.

The type of vehicles that can be used in the disclosed pharmaceutical compositions can vary. In some embodiments, the pharmaceutically acceptable vehicles are selected from binders, fillers and combinations thereof. In some embodiments, the pharmaceutically acceptable vehicle is selected from ascorbic acid, polyvinylpyrrolidone, polyvinylpyrrolidone K-30 (povidone K-30), glyceryl monostearate (GMS) or glyceryl monostearate salts, glyceryl behenate, glyceryl palmitostearate, hydroxypropyl cellulose, hydroxypropyl methylcellulose, methylcellulose, hydroxyethyl cellulose, sugars, dextran, cornstarch, dibasic calcium phosphate, dibasic calcium phosphate dihydrate, calcium sulfate, dicalcium phosphate, tricalcium phosphate, lactose, cellulose including microcrystalline cellulose, mannitol, sodium chloride, dry starch, pregelatinized starch, compressible sugar, mannitol, lactose monohydrate, starch, dibasic calcium phosphate dihydrate, calcium sulfate, dicalcium phosphate, tricalcium phosphate, powdered cellulose, microcrystalline cellulose, lactose, glucose, fructose, sucrose, mannose, dextrose, galactose, the corresponding sugar alcohols and other sugar alcohols, such as mannitol, sorbitol, xylitol, and combinations of any of the foregoing. In some embodiments, the pharmaceutically acceptable vehicle is polyvinylpyrrolidone K-30, also known as povidone K-30. In some embodiments, the pharmaceutically acceptable vehicle is polyvinylpyrrolidone K-30, also known as povidone K-30, having an average molecular weight of MW of 40,000 (CAS 9003-39-8). In some embodiments, the pharmaceutically acceptable vehicle is selected from glyceryl monostearate (GMS) or glyceryl monostearate salts, glyceryl behenate and glyceryl palmitostearate. In some embodiments, the pharmaceutically acceptable vehicle is glyceryl monostearate (GMS) or glyceryl monostearate salts. In some embodiments, the pharmaceutically acceptable vehicle is glyceryl behenate. In some embodiments, the pharmaceutically acceptable vehicle is glyceryl palmitostearate.

In some embodiments, the antioxidants prevent oxidation of the other components of the disclosed compositions. Oxidation can occur, for example, during sterilization where free radicals are generated. Addition of the antioxidants, or free radical scavengers, significantly reduces oxidation and makes the composition more pharmaceutically acceptable for use in subjects.

The type of antioxidants that can be used in the disclosed pharmaceutical compositions can vary. In some embodiments, the antioxidant is selected from methyl paraben and salts thereof, propyl paraben and salts thereof, vitamin E, vitamin E TPGS, propyl gallate, sulfites, ascorbic acid (aka L-ascorbic acid, also including the L-enantiomer of ascorbic acid, vitamin C), sodium benzoate, citric acid, cyclodextrins, peroxide scavengers, benzoic acid, ethylenediaminetetraacetic acid (EDTA) and salts thereof, chain terminators (e.g., thiols and phenols), butylated hydroxytoluene (BHT), butylated hydroxyanisole (BHA), and combinations thereof.

Uses or Methods of Treatment

The methods and compositions disclosed herein can be used to treat subjects suffering from neurodegenerative diseases, disorders, conditions, and symptoms for which inhibitors of CXXC5-DVL interface and/or GSK$\beta$ are known to provide or are later found to provide therapeutic benefit.

In some embodiments, methods disclosed herein include a method of treating a neurodegenerative disease or a clinical condition thereof, comprising administering to a subject at least one therapeutically effective dose of any of the compositions disclosed herein. The subject can be diagnosed with a clinical condition selected from and/or comprising dementia, Alzheimer's disease (AD), vascular dementia, senile dementia, frontotemporal dementia (FTD), Lewy body dementia (LBD), Parkinson's disease (PD), multiple system atrophy (MSA), corticobasal degeneration (CBD), progressive supranuclear palsy (PSP), Huntington's disease (HD), amyotrophic lateral sclerosis (ALS, or also known as Lou-Gehrig's disease), primary lateral sclerosis (PLS), progressive bulbar palsy (PBP), progressive muscular atrophy (PMA), pseudobulbar palsy, hereditary spastic paraplegia (HSP), cerebellar ataxia, Creutzfeldt-Jakob disease (CJD), multiple sclerosis (MS), and/or Guillain-Barré syndrome (GBS), and/or any other conditions associated with, induced by, or that are already resistant to drug treatments, therapies and/or surgical treatments. In certain embodiments, the methods disclosed herein further comprise administering to the subject at least one additional therapeutically effective dose of any of the compositions disclosed herein. In some embodiments, the at least one therapeutically effective dose of any of the compositions disclosed herein can be administered orally, parenterally, subcutaneously, intravenously, by inhalation and/or transdermally.

Yet other embodiments can include methods for reducing a side effect of a therapeutic regime, comprising administering to a subject at least one therapeutically effective dose of at least one agent that inhibits CXXC5-DVL interface in a subject and/or that enhances the expression and/or activity of GLP-1; wherein the subject has received at least one therapeutic regime comprising drug treatments, surgery, therapy, and wherein the subject experiences at least one side effect derived from the therapeutic regime. Consistent with these embodiments, side effects can include, but are not limited to, drug-resistance and/or relapse.

Kits

In a further aspect, kits are provided by the present disclosure, such kits comprising: one or more pharmaceutical compositions, each composition sterilized within a container, means for administration of the pharmaceutical compositions to a subject, and instructions for use.

Some embodiments include kits for carrying out the methods disclosed herein. Such kits typically comprise two or more components required for treating a clinical condition. Components of the kit include, but are not limited to, one or more of agents/compositions disclosed herein, reagents, containers, equipment and/or instructions for using the kit. Accordingly, the compositions and methods described herein can be performed by utilizing pre-packaged kits disclosed herein.

Examples

The following examples illustrate various aspects of the disclosure. It will be apparent to those skilled in the art that many modifications, both to materials and methods, can be practiced without departing from the scope of the disclosure.

CXXC5-type zinc finger protein 5 (CXXC5) is a negative feedback regulator of the Wnt/$\beta$-catenin pathway that functions via Disheveled (Dvl) binding. CXXC5 plays various pathophysiological roles involving regenerative tissue remodeling, especially at the specific pathophysiological status. However, the role of CXXC5 in the process of neurodegenerative diseases has not been defined yet. In the present disclosure, it was found unexpectedly that CXXC5 was highly expressed in brain tissues and/or peripheral blood of AD and/or PD patients, and thereby, experiencing reduced the expression of Wnt/$\beta$-catenin target genes such as GLP-1.

As disclosed herein, small molecules interfering CXXC-DVL protein-protein interaction (PPI) including, but are not limited to, A3334 and/or A3051, were identified and characterized as potential drugs that can improve expression and the activity of GLP-1 in patients diagnosed with AD and PD. The indirubin derivatives exerts these functions by activation of the Wnt/$\beta$-catenin signaling target genes involving metabolism including the GLP-1 via release of the negative feedback function of this pathway by CXXC5. Accordingly, the present disclosure relates to the use of indirubin analogs disclosed herein in inducing/activating GLP-1 in a subject, differentiating neural stem cells into dopamine producing neural cells and treating neurodegenerative diseases including AD and PD.

Bioinformatics data analysis. Cross-species comparison of CXXC5 and GLP-1 mRNA expression was performed in the space of molecular pathway gene sets from GEO databases and with statistically significant dysregulation defined by student's t-test in either of the two human Parkinson's disease and human/mouse Alzheimer's disease transcriptome datasets: normal (n=4) vs. Parkinson's disease patients (n=4) subjects, normal (n=13) vs. Alzheimer disease patients (n=13) subjects, and Control (n=7) vs. Pioglitazone (n=7).

Blood chemistry. Total blood of mice was collected by cardiac puncture. The blood was allowed to clot for 30 min and was then centrifuged for 30 min at 3,000×g to obtain supernatant to measure active GLP-1 concentration. ELISA assay kits were used to assess serum active GLP-1 (7-36).

Quantitative real-time polymerase chain reaction (PCR). Total RNA was extracted from ground tissue powder using TRIzol reagent (Invitrogen) according to the manufacturer's instructions. Reverse transcription was performed with M-MLV reverse transcriptase (Invitrogen) using 2 μg of total RNA. Synthesized cDNA was diluted to a concentration of 100 ng/μl. Quantitative PCR analyses were performed in the Rotor-gene Q real-time PCR cycler (Qiagen) using SYBR green reagent (Qiagen) with conditions of 95° C. for 10 min followed by 40 cycles at 95° C. for 5 s and 60° C. for 15 s. Relative quantification of mRNA levels was estimated using the comparative Ct method (ΔΔCt). Glp-1 mRNA values were normalized with respect to GAPDH.

Neural stem cell (NSCs) culture. NSCs were extracted from the forebrain of E14.5 rats and maintained in an undifferentiated state by culturing in medium containing 10 ng/ml of bFGF (Peprotech). Undifferentiated NSCs ($1 \times 10^5$) were treated with of each compound (10 μM) and cell morphology was assessed by capturing black and white images of the cells after 24 h.

Animals. The generation of Cxxc5$^{-/-}$ mice has been described previously. Cxxc5 heterozygous mice were intercrossed for four generations to obtain littermate wild-type and Cxxc5$^{-/-}$ mice and were maintained on a C57BL/6 background. Six-week-old Cxxc5$^{+/+}$ and Cxxc5$^{-/-}$ mice were fed HFD for 8 weeks. Wild-type male C57BL/6 mice (KOATECH, Seoul, Korea) were fed HFD consisting of 60% calories from fat (Research Diet, D12492) for 8 weeks. To validate that the insulin resistance mouse model was successfully established, fasting glucose levels were assessed with a One Touch Ultra glucometer (LifeScan). Subsequently, each HFD-fed mouse with a fasting glucose level higher than 16.7 mmol/L was orally administered A3334 (25 mg kg$^{-1}$), sitagliptin (50 mg kg$^{-1}$), or metformin (100 mg kg$^{-1}$) each day for 5 days at weeks 8 and 12. After the removal of the drugs, mice were maintained for 3 weeks on the HFD. To monitor pancreas regeneration, six-week-old Cxxc5$^{+/+}$ and Cxxc5$^{-/-}$ mice were fed an HFD as above. After dietary treatment for 4 weeks, the mice were intraperitoneally injected with STZ (50 mg/kg/d) for 1 week and the control group were injected with saline. After 2 weeks, Cxxc5$^{+/+}$ mice were administered A3334 or A3051 (25 mg kg$^{-1}$) and sitagliptin (50 mg kg$^{-1}$) per day by oral gavage for 4 weeks.

Dvl-CXXC5 in vitro binding assay. For the Dvl-CXXC5 in vitro binding assay, 100 μl of 5 mg/ml purified Dvl PDZ domain was added into 96-well Maxibinding Immunoplate (SPL) and incubated overnight in a 4° C. chamber. After washing with PBS, 10 μM PolyR-DBM[37] was added to each well and incubated for 3 h at room temperature. After washing with PBS, 100 μl of 1, 5, and 10 μM A3334 in PBS was added to each well and incubated for 1 h at room temperature. After washing with PBS three times, the fluorescence of each well was measured using a Fluorstar Optima microplate reader (BGM Lab Technologies). A3334 used in screening were designed and synthesized by Dr Gyoonhee Han (Yonsei University, Seoul, Korea).

Western blot assay. H4 and H4/SWE Cells were ground with a mortar and pestle before lysis in RIPA buffer (150 mM NaCl, 10 mM Tris, pH 7.2, 0.1% SDS, 1.0% Triton X-100, 1% sodium deoxycholate, and 5 mM EDTA). Samples were separated on 6-12% SDS polyacrylamide gels and transferred onto PROTRAN nitrocellulose membranes (Schleicher and Schuell Co.). The membranes were blocked with PBS containing 5% non-fat dry skim milk and 0.07% (vol/vol) Tween 20 and incubated with antibody specific for β-catenin (1:1,000, Santa Cruz Biotechnology, Inc.), CXXC5 (1:500, Santa Cruz Biotechnology, Inc.), p-GSK3β (S9) (1:500, Santa Cruz Biotechnology, Inc.). The membranes were then incubated with horseradish peroxidase-conjugated anti-rabbit (1:5,000, Bio-Rad Laboratories) or anti-mouse (1:5000, Cell Signaling Technology) IgG secondary antibody. Protein bands were visualized with enhanced chemiluminescence (GE Healthcare) using a luminescent image analyzer, LAS-3000 (Fujifilm). Western blot bands were analyzed using Multi-Gauge V3.0 software (Fujifilm).

Immunocytochemical analysis. H4 or H4/SWE cells treated with each compound were washed with PBS and fixed in 4% (wt/vol) paraformaldehyde (PFA) in PBS for 15 min at room temperature. The cells were then washed with PBS and permeabilized with 0.1% (vol/vol) Triton X-100 in PBS for 15 min. After washing with PBS, the cells were incubated with 10% bovine serum albumin (BSA) in PBS for 30 min and then with antibodies specific for β-catenin (1:100; BD) overnight at 4° C. The cells were washed in PBS and incubated with Alexa Fluor 488—conjugated IgG secondary antibody (1:400; Molecular Probes) at room temperature for 1 h. Cell nuclei were counterstained with DAPI for 10 min and the stained samples were examined under a LSM510 META microscope.

Human Aβ42 ELISA assay. H4 or H4/SWE cells were cultured in Dulbecco's Modified Eagle's Medium (DMEM, Gibco) containing 10% fetal bovine serum (FBS) and grown to confluence in a 5% $CO_2$ and 95% air humidified atmosphere. The cells were seeded in 6-well plate in DMEM supplemented with 10% FBS and allowed to adhere overnight. The cells were treated with each compound (1~20 uM) for 24 h and collected in 1 ml of medium. The samples were treated with protease inhibitor cocktail (PIC) to avoid the degradation of Amyloid β by protease and centrifuged at 3000 rpm for 3 min. Experiments were performed according to the guidance of Human Aβ42 ELISA Kit protocol (Invitrogen). The amount of secreted Amyloid β was normalized by measuring total protein concentration.

Statistical analysis. Data are presented as means±standard deviation (SD). Statistical analyses were performed using unpaired two-tailed Student's t-test. Asterisks denote statistically significant differences (*, P<0.05; , P<0.01; *, P<0.005).

5,6-dichloroindirubin-3'-methoxime (A3051)

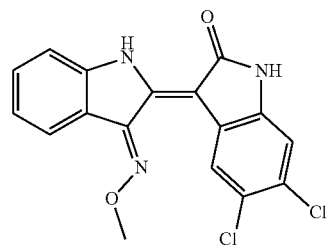 [SMILES: CO/N=C1/C(=C2/C(=O)Nc3cc(Cl)c(Cl)cc32)Nc2ccccc21]

| 33 | 34 |
|---|---|
| 5-methoxylindirubin-3'-oxim (A3334) | 5,6-dichloroindirubin-3'-propyloxim (A3486) |
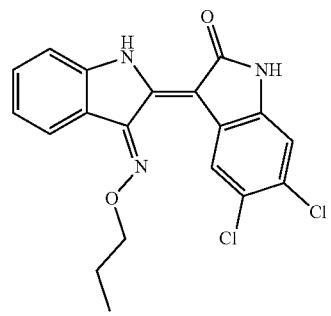
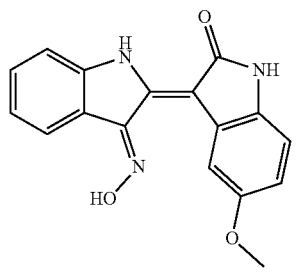 [SMILES: COc1ccc2c(c1)/C(=C1/Nc3ccccc3/C1=N\O)C(=O)N2]
Indirubin-3'-oxime (I3O or IO)
5.6-chloroindirubin-3'-benzyloxime (A3538)
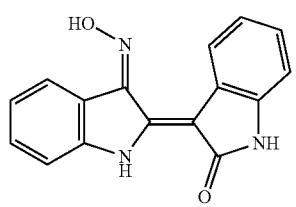 [SMILES: O=C1Nc2ccccc2/C1=C1/Nc2ccccc2/C1=N\O]
6-Bromoindirubin-3'-oxime (BIO)
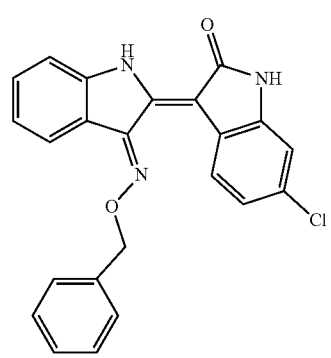
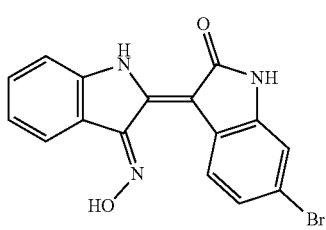 [SMILES: O=C1Nc2cc(Br)ccc2/C1=C1/Nc2ccccc2/C1=N\O]
Indirubin
(Z)-5'-bromo-6'-nitro-[2,3'-biindolinylidene]-2',3-dione (A2785)
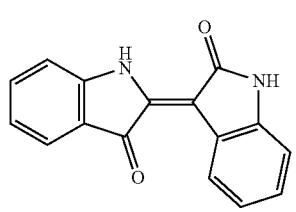 [SMILES: O=C1Nc2ccccc2/C1=C1/Nc2ccccc2C1=O]
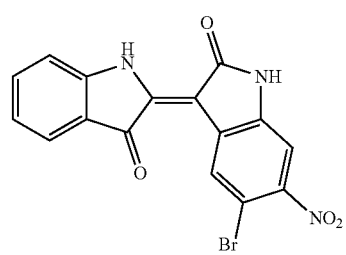 [SMILES: O=C1Nc2cc([N+](=O)[O-])c(Br)cc2/C1=C1/Nc2ccccc2C1=O]

6-Nitro-5-trifuloromethoxyindirubin-3'-methoxime (A2794)

5-trifluoromethoxyindirubin-3'-benzyloxime (A4735)

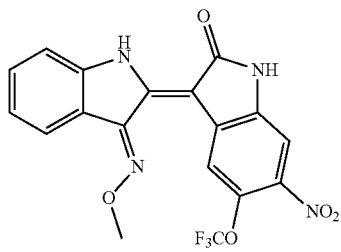 [SMILES: CO/N=C1/C(=C2/C(=O)Nc3cc([N+](=O)[O-])c(OC(F)(F)F)cc32)Nc2ccccc21]

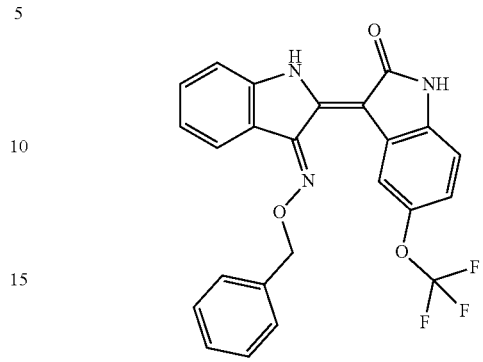

5-trifluoromethoxyindirubin-3'-ehtyloxime (A4733)

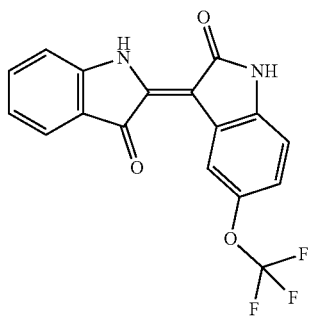 [SMILES: O=C1Nc2ccc(OC(F)(F)F)cc2/C1=C1/Nc2ccccc2C1=O]

Screening for compounds that inhibit the CXXC5-DVL interaction. To initially identify small molecules that inhibited the CXXC5-DVL interaction, chemical libraries (2,280 compounds: 1,000 from ChemDiv and 1,280 from SigmaLOPAC) were screened by in vitro binding assay that was previously described. See e.g., Kim et al. (2015) *CXXC5 is a negative-feedback regulator of the Wnt/beta-catenin pathway involved in osteoblast differentiation.* CELL. DEATH. DIFFER. 22, 912-920. Briefly, 5 mg/ml purified DVL-PDZ domain was incubated in each well of a 96-well Maxibinding Immunoplate (SPL, Seoul, Korea) at 4° C. for 16 h. After the addition of 10 μM FITC-tagged PTD-DBMP to each well, each compound in the chemical library or control (DMSO) was treated to the well at a final concentration of 30 μM. The fluorescence intensity was measured using a Fluorstar Optima microplate reader (BGM Lab Technologie, Ortenberg, Germany) and normalized as follows: "('compounds-treated group'–'blank')/('DMSO-treated control'–'blank')*100".

Nineteen compounds were selected as initial hits which suppress the CXXC5-DVL (PZD-DVL-PTD-DBMP (FITC) interaction more than 90%, and their capabilities of activation of the Wnt/β-catenin pathway was confirmed by using the HEK293 cells harboring the pTOPFlash reporter in its chromosome. Among these compounds, indirubin analogs including BIO and I3O were identified. A summary of the high-throughput screening results is provided in Table 1.

TABLE 1

Summary of high-throughput screening results

| Category | Parameter | Description |
|---|---|---|
| Assay | Type of assay | In vitro binding assay |
| | Target | CXXC5-DVL interaction |
| | Primary measurement | Fluorescence intensity |
| | Key reagents | FITC-tagged PTD-DBM peptide and DVL-PZD domain protein |
| | Assay protocol | The protocol was provided in "Small molecule inhibitors of the Dishevelled-CXXC5 interaction are new drug candidates" |
| Library | Library size | 2280 compounds assayed in 96-well plates as single compounds at 10 mM in DMSO |
| | Library composition | Small molecules |
| | Source | ChemDiv and Sigma LOPAC 1280 |
| Screen | Format | 96-well black polystyrene plates |
| | Concentration(s) tested | Constant 30 μM concentration, 0.3% DMSO |
| | Plate controls | DMSO-treated group |
| | Reagent/compound dispensing system | Reagents and compounds were dispensed manually |
| | Detection instrument and software | FLUOstar OPTIMA (BMG LABTECH) |

TABLE 1-continued

Summary of high-throughput screening results

| Category | Parameter | Description |
|---|---|---|
| | Assay validation/QC | Z-factor > 0.7 |
| | Correction factors | N/A |
| | Normalization | The sample result was normalized to positive control and is represented as % CXXC5-DVL interaction |
| Post-HTS analysis | Hit criteria | <10% inhibition |
| | Hit rate | 1% |

TABLE 2

List of top-ranked compounds screened through an in vitro CXXC5-DVL PPI inhibition assay using chemical libraries that includes 2,280 small molecules

| Compound | Structure | Empirical Formula | CXXC5-DVL inhibitory activity (%) |
|---|---|---|---|
| 1 | 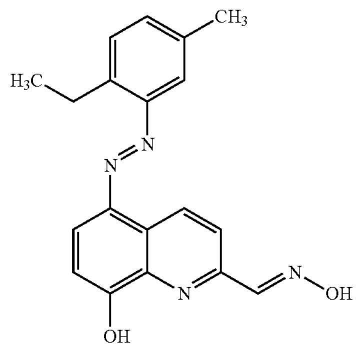 [SMILES: CCc1ccc(C)cc1/N=N/c1ccc(O)c2nc(/C=N/O)ccc12] | $C_{18}H_{16}N_4O_3$ | 85.25 |
| 2 | 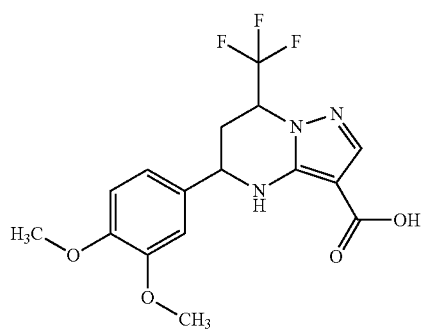 [SMILES: COc1ccc(C2CC(C(F)(F)F)n3ncc(C(=O)O)c3N2)cc1OC] | $C_{16}H_{16}F_3N_3O_4$ | 90.63 |
| 3 | 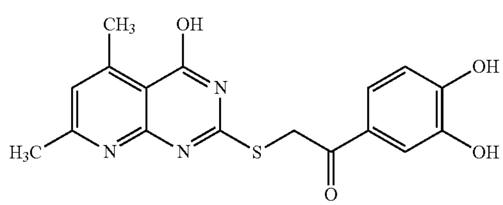 [SMILES: Cc1cc(C)c2c(O)nc(SCC(=O)c3ccc(O)c(O)c3)nc2n1] | $C_{17}H_{15}N_3O_4S$ | 88.19 |
| 4 | 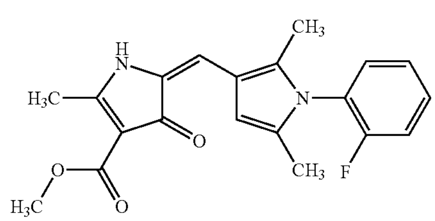 [SMILES: COC(=O)C1=C(C)N/C(=C/c2cc(C)n(-c3ccccc3F)c2C)C1=O] | $C_{20}H_{19}FN_2O_3$ | 87.58 |

TABLE 2-continued

List of top-ranked compounds screened through an in vitro CXXC5-DVL PPI inhibition assay using chemical libraries that includes 2,280 small molecules

| Compound | Structure | Empirical Formula | CXXC5-DVL inhibitory activity (%) |
|---|---|---|---|
| 5 | 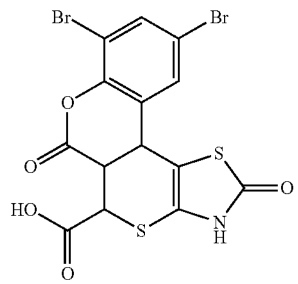 [SMILES: O=C(O)C1Sc2[nH]c(=O)sc2C2c3cc(Br)cc(Br)c3OC(=O)C12] | $C_{14}H_7Br_2NO_5S_2$ | 90.48 |
| 6 | 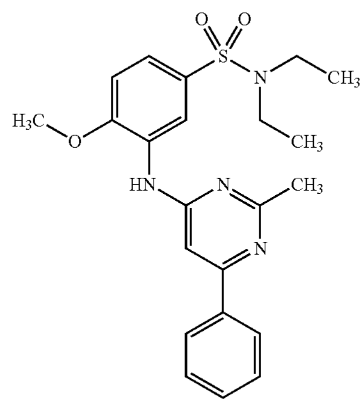 [SMILES: CCN(CC)S(=O)(=O)c1ccc(OC)c(Nc2cc(-c3ccccc3)nc(C)n2)c1] | $C_{22}H_{26}N_4O_3S$ | 58.24 |
| 7 | 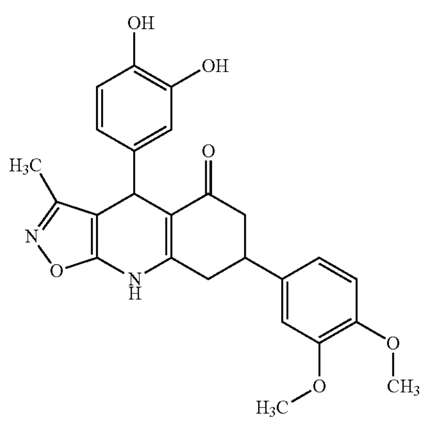 [SMILES: COc1ccc(C2CC(=O)C3=C(C2)Nc2onc(C)c2C3c2ccc(O)c(O)c2)cc1OC] | $C_{25}H_{24}N_2O_6$ | 90.87 |
| 8 | 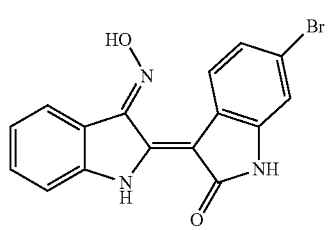 [SMILES: O=C1Nc2cc(Br)ccc2/C1=C1/Nc2ccccc2/C1=N\O] | $C_{16}H_{10}BrN_3O_2$ | 103 |

TABLE 2-continued
List of top-ranked compounds screened through an in vitro CXXC5-DVL PPI inhibition
assay using chemical libraries that includes 2,280 small molecules
| Compound | Structure | Empirical Formula | CXXC5-DVL inhibitory activity (%) |
|---|---|---|---|
| 9 | 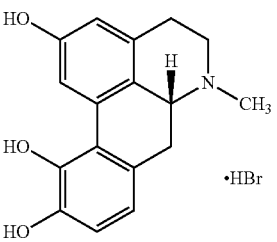 | $C_{17}H_{17}NO_3 \cdot HBr$ | 89.41 |
| 10 | 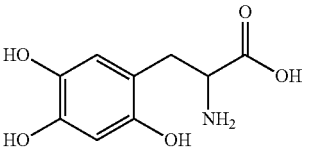 [SMILES: NC(Cc1cc(O)c(O)cc1O)C(=O)O] | $C_9H_{11}NO_5$ | 90.32 |
| 11 | 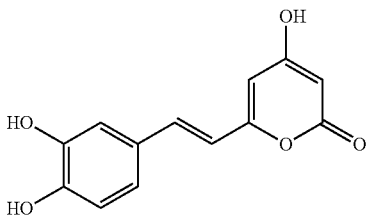 [SMILES: O=c1cc(O)cc(/C=C/c2ccc(O)c(O)c2)o1] | $C_{13}H_{10}O_5$ | 90.05 |
| 12 | 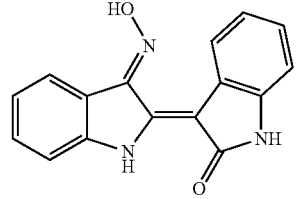 [SMILES: O=C1Nc2ccccc2/C1=C1/Nc2ccccc2/C1=N\O] | $C_{16}H_{11}N_3O_2$ | 89 |
| 13 | 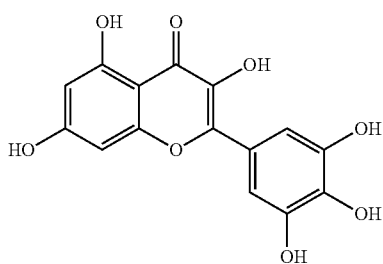 [SMILES: O=c1c(O)c(-c2cc(O)c(O)c(O)c2)oc2cc(O)cc(O)c12] | $C_{15}H_{10}O_8$ | 85.22 |
| 14 | 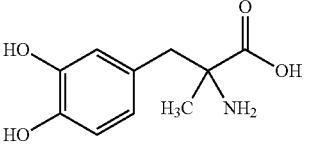 | $C_{10}H_{13}NO_4$ | 85.22 |
| 15 | 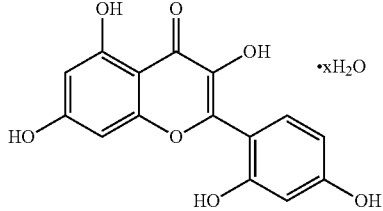 [SMILES: O=c1c(O)c(-c2ccc(O)cc2O)oc2cc(O)cc(O)c12] | $C_{15}H_{10}O_7 \cdot xH_2O$ | 85.41 |

TABLE 2-continued

List of top-ranked compounds screened through an in vitro CXXC5-DVL PPI inhibition assay using chemical libraries that includes 2,280 small molecules

| Compound | Structure | Empirical Formula | CXXC5-DVL inhibitory activity (%) |
|---|---|---|---|
| 16 | [structure] | $C_{23}H_{27}N_3O_7 \cdot HCl$ | 87.9 |
| 17 | [structure] | $C_{14}H_{12}O_4$ | 85.25 |
| 18 | [structure] | $C_{19}H_{27}NO_3 \cdot HCl$ | 86.81 |
| 19 | [structure] | $C_{34}H_{34}N_4O_4$ | 89.44 |

Figure 11:
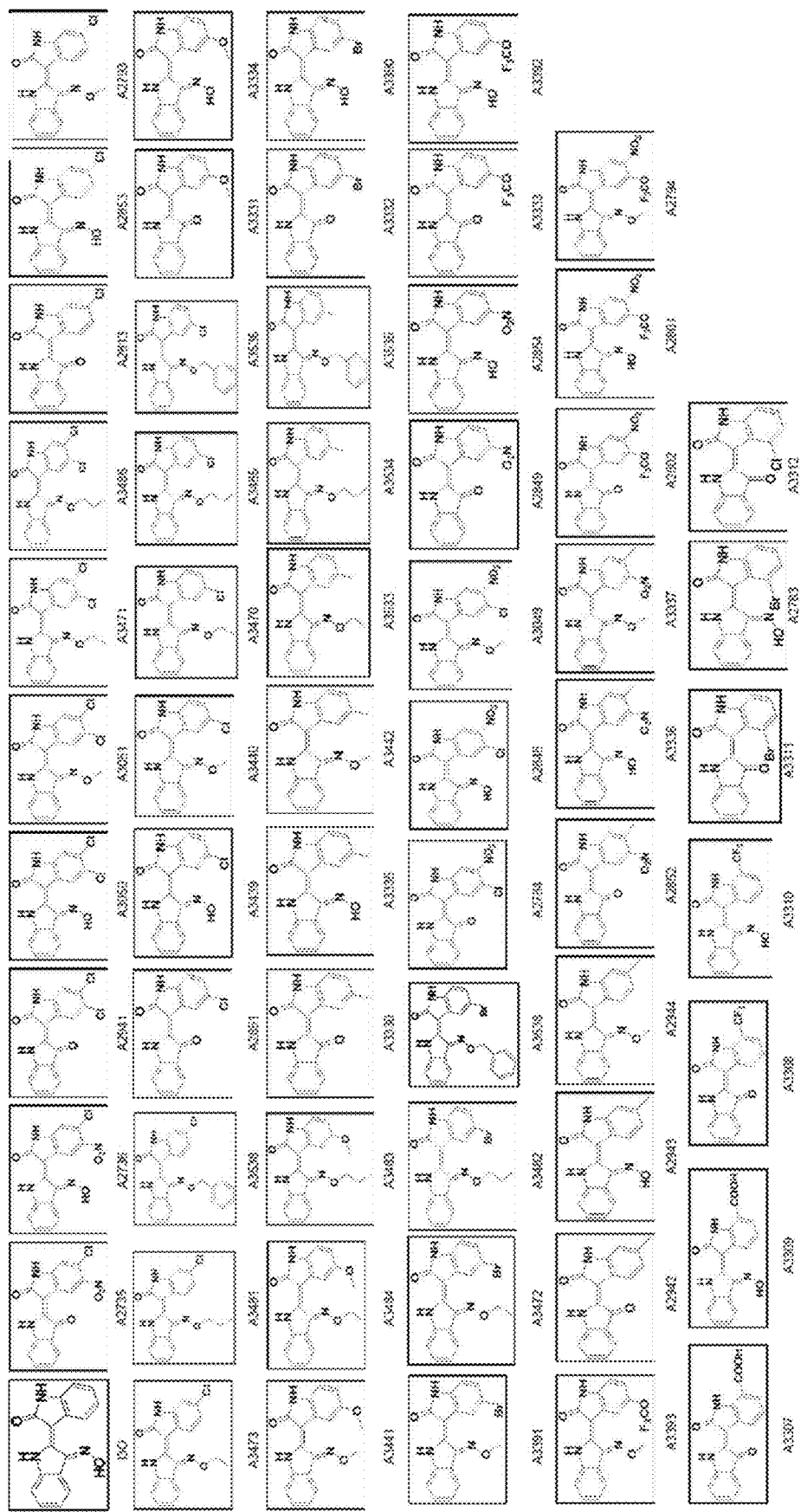
FIG. 11. Chemical structures of examples of indirubin analogs disclosed herein.
Figure 12:
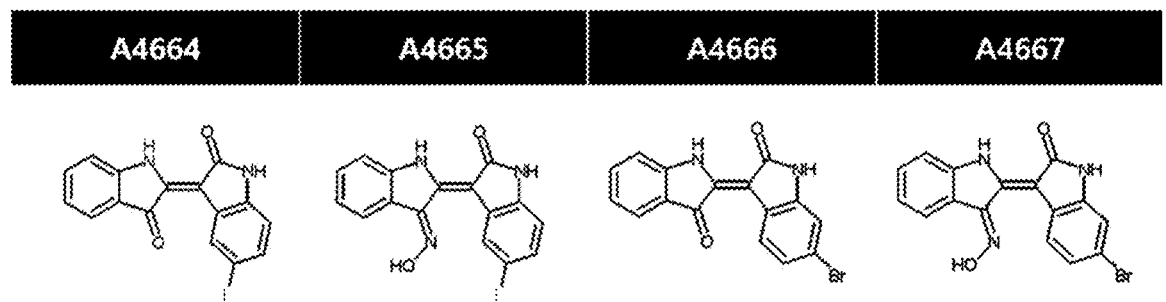
FIG. 12. Chemical structures of examples of indirubin analogs disclosed herein.

Indirubin analog compounds (#8 and #12; Table 2) were repeatedly identified as CXXC5-DVL inhibitors and showed effectiveness in the activation of Wnt/β-catenin pathway using reporter assay. To obtain functionally improved compound, about 60 indirubin derivatives were newly synthesized by replacing the functional groups at the $R_1$ and $R_2$ sites of the indirubin backbone based on the structure of indribin-3'-oxim (I3O) (#12; Table 2). Newly synthesized indirubin derivatives are described in Tables 3-5 and the structures of these compounds are shown FIG. 11 and FIG. 12.

TABLE 3

List of chemically synthesized compounds shown to at least partially inhibit the activity of CXXC5-DVL. C: control

|   | Compound # | IUPAC name | R1 4 | R1 5 | R1 6 | R1 7 | R2 3' |
|---|---|---|---|---|---|---|---|
| C | Indirubin | Indirubin | H | H | H | H | O |
| 1 | A2735 | 6-Chloro-5-nitroindirubin | H | $NO_2$ | Cl | H | O |
| 2 | A2736 | 6-Chloro-5-nitro indirubin-3'-oxime | H | $NO_2$ | Cl | H | NOH |
| 3 | A2941 | 5,6-dichloroindirubin | H | Cl | Cl | H | O |
| 4 | A3050 | 5,6-dichloroindirubin-3'-oxime | H | Cl | Cl | H | NOH |
| 5 | A3051 | 5,6-dichloroindirubin-3'-methoxime | H | Cl | Cl | H | $NOCH_3$ |
| 6 | A3471 | 5,6-dichloroindirubin-3'-ethyloxime | H | Cl | Cl | H | $NOCH_2CH_3$ |
| 7 | A3486 | 5,6-dichloroindirubin-3'-propyloxime | H | Cl | Cl | H | $NOCH_2CH_2CH_3$ |
| 8 | A2813 | 6-Chloroindirubin | H | H | Cl | H | O |
| 9 | A2853 | 6-Chloroindirubin-3'-oxime | H | H | Cl | H | NOH |
| 10 | A2793 | 6-Chloroindirubin-3'-methoxime | H | H | Cl | H | $NOCH_3$ |
| 11 | A3473 | 6-Chloroindirubin-3'-ethyloxime | H | H | Cl | H | $NOCH_2CH_3$ |
| 12 | A3481 | 6-Chloroindirubin-3'-propyloxime | H | H | Cl | H | $NOCH_2CH_2CH_3$ |
| 13 | A3538 | 6-Chloroidirubin-3'-benzyloxime | H | H | Cl | H | $NOCH_2Ph$ |
| 14 | A2851 | 5-Chloroindirubin | H | Cl | H | H | O |
| 15 | A3439 | 5-Chloroindirubin-3'-oxime | H | Cl | H | H | NOH |
| 16 | A3440 | 5-Chloroindirubin-3'-methoxime | H | Cl | H | H | $NOCH_3$ |
| 17 | A3470 | 5-Chloroindirubin-3'-ethyloxime | H | Cl | H | H | $NOCH_2CH_3$ |
| 18 | A3485 | 5-Chloroindirubin-3'-propyloxime | H | Cl | H | H | $NOCH_2CH_2CH_3$ |
| 19 | A3536 | 5-Chloroindirubin-3'-benzyloxime | H | Cl | H | H | $NOCH_2Ph$ |
| 20 | A3331 | 5-Methoxyindirubin | H | $OCH_3$ | H | H | O |
| 21 | A3334 | 5-Methoxyindirubin-3'-oxime | H | $OCH_3$ | H | H | NOH |
| 22 | A3441 | 5-Methoxyindirubin-3'-methoxime | H | $OCH_3$ | H | H | $NOCH_3$ |
| 23 | A3484 | 5-Methoxy indirubin-3'-ethyloxime | H | $OCH_3$ | H | H | $NOCH_2CH_3$ |
| 24 | A3483 | 5-Methoxyindirubin-3'-proyloxime | H | $OCH_3$ | H | H | $NOCH_2CH_2CH_2$ |
| 25 | A3330 | 5-Methylindirubin | H | $CH_3$ | H | H | O |
| 26 | A3335 | 5-Methylindirubin-3'-oxime | H | $CH_3$ | H | H | NOH |
| 27 | A3442 | 5-Methylindirubin-3'-methoxime | H | $CH_3$ | H | H | $NOCH_3$ |
| 28 | A3533 | 5-Methylindirubin-3'-ethyloxime | H | $CH_3$ | H | H | $NOCH_2CH_3$ |
| 29 | A3534 | 5-Methylindirubin-3'-propyloxime | H | $CH_3$ | H | H | $NOCH_2CH_2CH_2$ |
| 30 | A3535 | 5-Methylindirubin-3'-benzyloxime | H | $CH_3$ | H | H | $NOCH_2Ph$ |

TABLE 4

List of chemically synthesized compounds shown to at least partially inhibit the activity of CXXC5-DVL. C: control

|   | Compound # | IUPAC name | R1 4 | R1 5 | R1 6 | R1 7 | R2 3' |
|---|---|---|---|---|---|---|---|
| C | I3O | Indirubin-3'-oxime | H | H | H | H | NOH |
| 31 | A3332 | 5-Bromoindirubin | H | Br | H | H | O |
| 32 | A3390 | 5-bromoindirubin-3'-oxime | H | Br | H | H | NOH |
| 33 | A3391 | 5-bromoindirubin-3'-methoxime | H | Br | H | H | $NOCH_3$ |
| 34 | A3472 | 5-bromoindirubin-3'-ethyloxime | H | Br | H | H | $NOCH_2CH_3$ |
| 35 | A3482 | 5-bromoindirubin-3'-propyloxime | H | Br | H | H | $NOCH_2CH_2CH_3$ |
| 36 | A3537 | 5-bromoindirubin-3'-benzyloxime | H | Br | H | H | $NOCH_2Ph$ |
| 37 | A2784 | 5-Chloro-6-nitroindirubin | H | Cl | $NO_2$ | H | O |
| 38 | A2848 | 5-Cl-6-nitroindirubin-3'-oxime | H | Cl | $NO_2$ | H | NOH |
| 39 | A3049 | 5-Chloro-6-nitroindirubin-3'-methoxime | H | Cl | $NO_2$ | H | $NOCH_3$ |
| 40 | A2849 | 5-Nitroindirubin | H | H | $NO_2$ | H | O |
| 41 | A2854 | 5-Nitroindirubin-3'-oxime | H | H | $NO_2$ | H | NOH |
| 42 | A3333 | 5-Trifluoromethoxyindirubin | H | $OCF_3$ | H | H | O |
| 43 | A3392 | 5-Trifluoromethoxyindirubin | H | $OCF_3$ | H | H | NOH |
| 44 | A3393 | 5-Trifluoromethoxyindirubin-3'-methoxime | H | $OCF_3$ | H | H | $NOCH_3$ |
| 45 | A2942 | 6 -Methylindirubin | H | H | $CH_3$ | H | O |
| 46 | A2943 | 6-Methylindirubin-3'-oxime | H | H | $CH_3$ | H | NOH |
| 47 | A2944 | 6-Methylindirubin-3'-methoxime | H | H | $CH_3$ | H | $NOCH_3$ |
| 48 | A2852 | 6-Methyl-5-nitroindirubin | H | $NO_2$ | $CH_3$ | H | O |
| 49 | A3336 | 6-Methyl-5-nitroindirubin-3'-oxime | H | $NO_2$ | $CH_3$ | H | NOH |
| 50 | A3337 | 6-Methyl-5-nitroindirubin-3'-methoxime | H | $NO_2$ | $CH_3$ | H | $NOCH_3$ |
| 51 | A2802 | 6-Nitro-5-Trifluoromethoxyindirubin | H | $OCF_3$ | $NO_2$ | H | O |
| 52 | A2801 | 6-Nitro-5-trifluoromethoxyindirubin-3'-oxime | H | $OCF_3$ | $NO_2$ | H | NOH |
| 53 | A2794 | 6-Nitro-5-trifluoromethoxyindirubin-3'-methoxime | H | $OCF_3$ | $NO_2$ | H | $NOCH_3$ |
| 54 | A3307 | Indirubin-7-carboxylic acid | H | H | H | COOH | O |
| 55 | A3309 | Indirubin-7-carboxylic acid-3'-oxime | H | H | H | COOH | NOH |
| 56 | A3308 | 7-Trifluoromethylindirubin | H | H | H | $CF_3$ | O |
| 57 | A3310 | 7-Trifluoromethylindirubin-3'-oxime | H | H | H | $CF_3$ | NOH |
| 58 | A3311 | 4-Bromoindirubin | Br | H | H | H | O |

TABLE 4-continued

List of chemically synthesized compounds shown to at least partially inhibit the activity of CXXC5-DVL. C: control

| | | | R1 | | | | R2 |
|---|---|---|---|---|---|---|---|
| | Compound # | IUPAC name | 4 | 5 | 6 | 7 | 3' |
| 59 | A2783 | 4-Bromoindirubin-3'-oxime | Br | H | H | H | NOH |
| 60 | A3312 | 4-Chloroindirubin | H | H | H | H | O |

TABLE 5

List of chemically synthesized compounds shown to at least partially inhibit the activity of CXXC5-DVL

| No. | Compound # | IUPAC Name | 3' moiety |
|---|---|---|---|
| 1 | A4664 | 5-Fluoroindirubin | O |
| 2 | A4665 | 5-Fluoroindirubin-3'-oxime | NOH |
| 3 | A4666 | 6-Bromoindirubin | O |
| 4 | A4667 | 6-Bromoindirubin-3'-oxime | NOH |

The Wnt/β-catenin pathway plays a role in the pathological process, and its response genes can be used as therapeutic targets for the metabolic diseases. CXXC5-type zinc finger protein 5 (CXXC5), a negative regulator of the Wnt/β-catenin pathway functioning via Disheveled (Dvl) binding. As provided herein, the functional role of CXXC5 in neurodegenerative diseases and the relationship between CXXC5 and Wnt/β-catenin signaling were investigated in human brain tissue, blood, and a mouse model. CXXC5 is unexpectedly overexpressed in brain and central nervous systems in AD and/or PD patients.

Relative mRNA expression of GLP-1 and other Wnt/β-catenin signaling target genes in Cxxc5$^{-/-}$ mice fed a high-fat diet (HFD) were increased. These results provided herein suggest CXXC5 as a therapeutic target for treatment of neurodegenerative diseases. A small molecule inhibiting the CXXC5-Dvl interaction restored the phenotypes as observed in HFD-fed Cxxc5$^{-/-}$ mice. Administration of at least one of compounds and/or compositions described herein increased serum active GLP-1 levels of HFD-fed mice. In contrast to the effect of the DDP-4 inhibitor sitagliptin, the increase in serum active GLP-1 levels were significantly higher in HFD-fed, STZ-induced diabetes mice. Overall, inhibition of CXXC5 activity by a small molecule-mediated interference of Dvl binding can be a potential therapeutic approach for the treatment of neurodegenerative diseases including AD and PD.

Figure 1B:
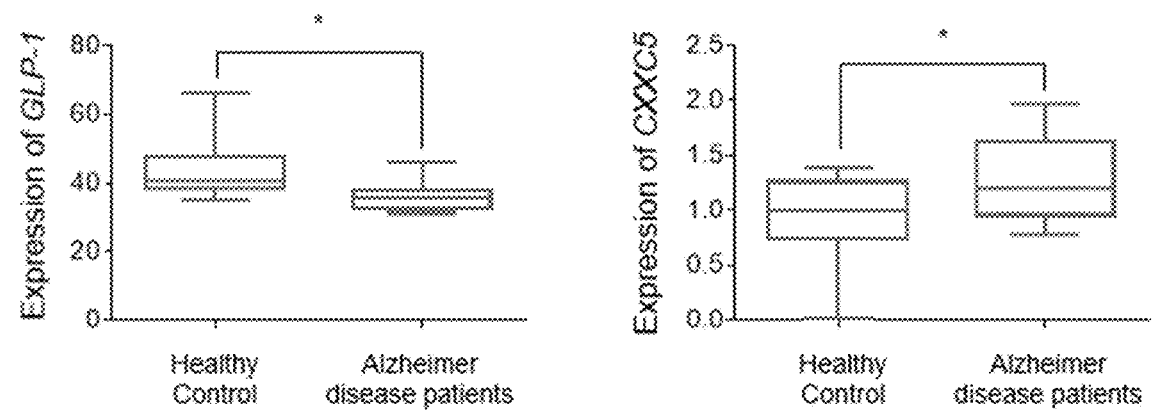
FIG. 1B. Graphs illustrating the mRNA expression levels of GLP-1 and CXXC5 in the peripheral blood of untreated patients with stage 1 Alzheimer's disease (AD) compared to the normal healthy control (mean±s.e.m., n=13, *P<0.05).
Figure 1C:
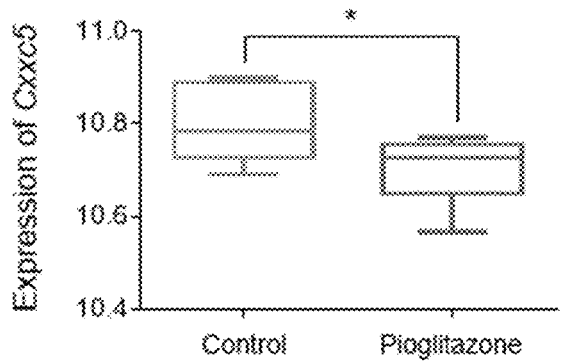
FIG. 1C. Graph illustrating the effect of pioglitazone, an anti-diabetes drug, on the expression of CXXC5 in a transgenic Alzheimer's disease mouse model (mean±s.e.m., n=7, *P<0.05).

Elevated CXXC5 levels and reduced GLP-1 levels in the brains of patients diagnosed with Alzheimer's and/or Parkinson's disease. Referring now to FIG. 1A-1B, the expression of CXXC5 was significantly increased in the peripheral blood or blood mononuclear cells of the patients diagnosed with AD or PD while the expression of GLP-1 in these patients were significantly lower than the healthy control. Pioglitazone, a diabetes drug designed to control CEBPα/PPARβ, suppressed the expression of CXXC5, indicating that inhibitory effect by CXXC5 overexpression in the neurodegenerative diseases can be suppressed by controlling diabetes (FIG. 1C). Overall, these results provide that GLP-1 expression can be suppressed by CXXC5 overexpression, which inhibits the Wnt/β-catenin pathway by the mechanism of CXXC5-DVL PPI.

Figure 2A:
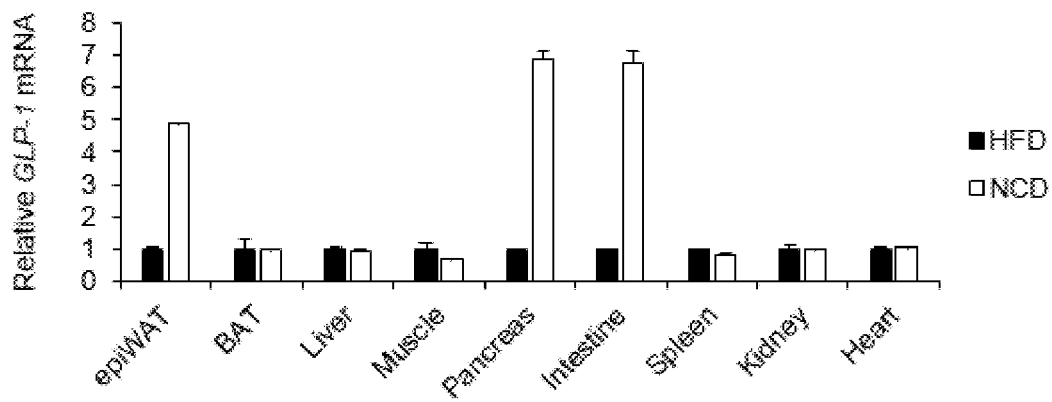
FIG. 2A. Graph illustrating relative GLP-1 mRNA expression in various types of tissues (epiWAT, BAT, liver, muscle, pancreas, intestine spleen, kidney, and heart) in mice that were on high fat diet (HFD) or normal chow diet (NCD).
Figure 2B:
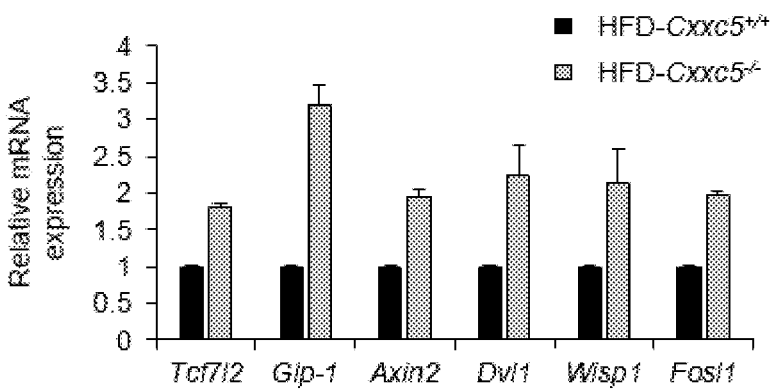
FIG. 2B. Graphs illustrating relative expression levels of GLP-1 and other Wnt/β-catenin signaling target genes (Tcf7l2, Axin2, Dvl1, Wisp1, and Fosl1) in epiWAT of $Cxxc5^{+/+}$ and $Cxxc5^{-/-}$ mice that were on high fat diet (HFD).
Figure 2C:
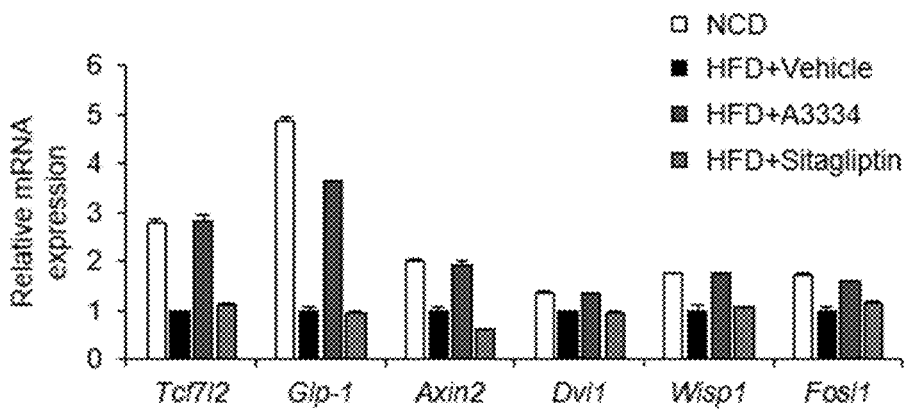
FIG. 2C. Graphs illustrating relative expression levels of GLP-1 and other Wnt/β-catenin signaling target genes (Tcf7l2, Axin2, Dvl1, Wisp1, and Fosl1) in NCD-mice and HFD-mice that were treated with vehicle, A3334, and sitagliptin.

GLP-1 mRNA expression is lower in epididymal white adipose tissue (epiWAT), pancreas, and intestine of the mice fed with HFD compared to the mice fed with normal Chow diet (NCD). Referring now to FIG. 2A-2C, relative expression levels of GLP-1 and other Wnt/β-catenin signaling target genes (Tcf712, Axin2, Dvl1, Wisp1, and Fosl1) in epiWAT were reduced when Cxxc5$^{+/+}$ mice were fed on high fat diet (HFD) as compared to those in Cxxc5$^{+/+}$ mice on normal Chow diet (NCD). When Cxxc5$^{-/-}$ mice were fed on HFD, the relative expression levels of GLP-1 and other Wnt/β-catenin signaling target genes (Tcf712, Axin2, Dvl1, Wisp1, and Fosl1) in epiWAT were restored (FIG. 2B). Treatment with A3334 restored the phenotypes as observed in HFD-fed Cxxc5$^{-/-}$ mice while the sitagliptin treatment did not (FIG. 2C).

Figure 3A:
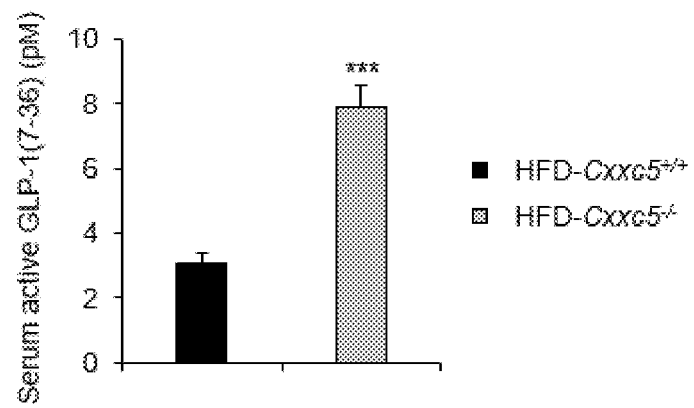
FIG. 3A. Graph illustrating the serum active GLP-1 levels in $Cxxc5^{+/+}$ and $Cxxc5^{-/-}$ mice that were on high fat diet (HFD).
Figure 3B:
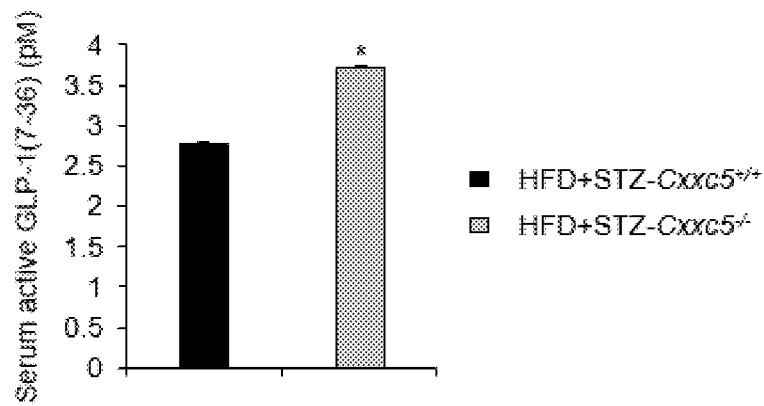
FIG. 3B. Graph illustrating the serum active GLP-1 levels in HFD-fed, streptozotocin (STZ)-induced diabetes $Cxxc5^{+/+}$ mice and HFD-fed, STZ-induced diabetes $Cxxc5^{-/-}$ mice.
Figure 4A:
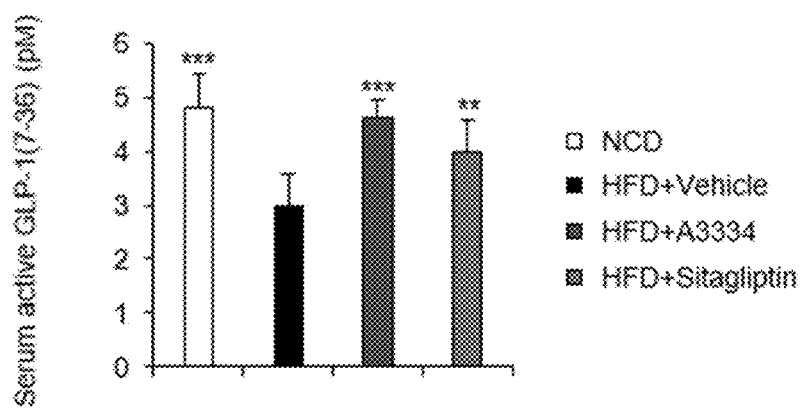
FIG. 4A. Graph illustrating the serum active GLP-1 levels in NCD-mice and HFD-mice that were treated with vehicle, A3334, and sitagliptin.
Figure 4B:
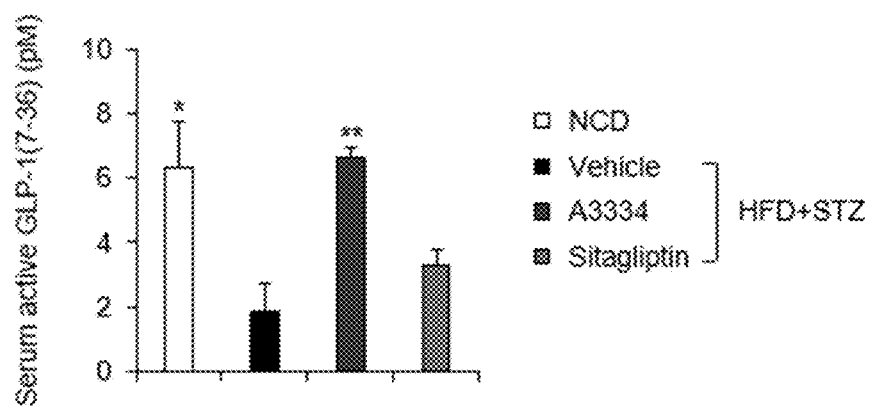
FIG. 4B. Graph illustrating the serum active GLP-1 levels in HFD-fed, STZ-induced diabetes that were treated with vehicle, A3334, and sitagliptin.

Serum active GLP-1 level was restored in Cxxc5$^{-/-}$ HFD-mice or STZ induced Cxxc5$^{-/-}$ HFD-mice. Diabetes is one of the major metabolic diseases and the current clinically available drugs including sulfonylureas, SGLT2 inhibitors, PPARγ agonists, DPP4 inhibitors, and biguanides can control blood glucose levels by acting on peripheral insulin target tissues such as the pancreas, intestine, muscle, and liver. One example of drug candidates, A3334, which restores the suppressed Wnt/β-catenin pathway in the diet-induced obesity and diabetes models, showed an initial temporal effect similar to that of the major anti-diabetes drugs, the DPP4 inhibitor sitagliptin and the biguanide medication metformin (data not shown). Referring now to FIG. 3A-3B, low serum active GLP-1 levels induced by HFD were restored in both Cxxc5$^{-/-}$ mice and STZ-induced diabetic Cxxc5$^{-/-}$ mice. The A3334 treatment in both HFD-mice and STZ-induced diabetic HFD-mice restored the serum active GLP-1 levels to the levels comparable to the mice fed on NCD. Sitagliptin, the anti-diabetes drug designed stabilize GLP-1 by DPP4 inhibition, was also used as a positive control. The A3334 treatment significantly rescued (increased) active GLP-1 expression in blood serum when compared to the effect observed from the sitagliptin treatment.

Figure 5:
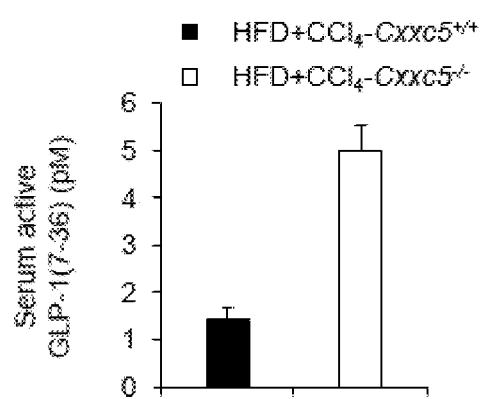
FIG. 5. Graph illustrating the serum active GLP-1 levels in HFD-fed, $CCl_4$-induced NASH $Cxxc5^{+/+}$ mice and HFD-fed, $CCl_4$-induced NASH $Cxxc5^{-/-}$ mice.
Figure 6A:
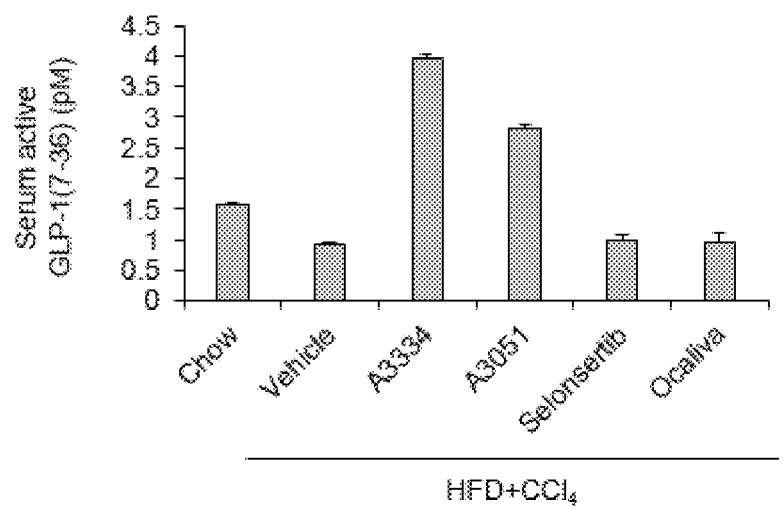
FIG. 6A. Graph illustrating the serum active GLP-1 levels in NCD-mice ("Chow") and RFD-fed, STZ-induced NASH mice that were treated with vehicle, A3334, A3051, selonsertib, and ocaliva.
Figure 6B:
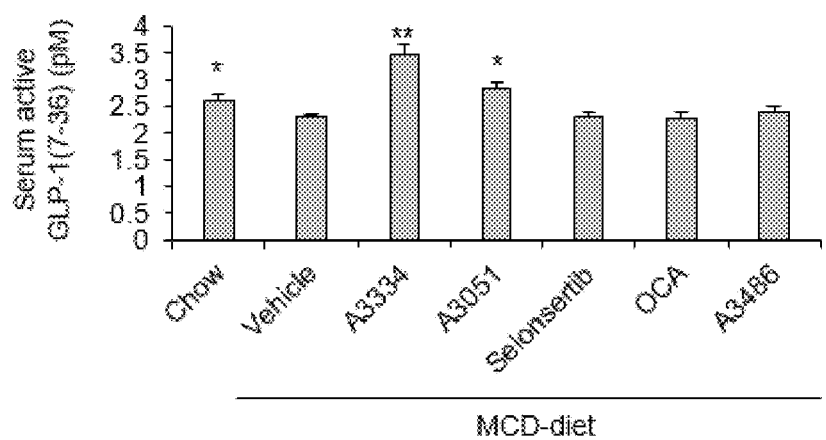
FIG. 6B. Graph illustrating the serum active GLP-1 levels in NCD-mice ("Chow") and RFD-fed, methionine-choline deficient diet (MCD)-induced NASH mice that were treated with vehicle, A3334, A3051, selonsertib, ocaliva ("OCA"), and A3486.

Serum active GLP-1 level was restored in CCl$_4$ induced Cxxc5$^{-/-}$ HFD-mice. Referring now to FIG. 5, HFD and CCl$_4$ induced suppression of serum active GLP-1 level was restored by the CXXC5 knock out in a NASH mouse model. The treatment with A3334 or A3051 significantly rescued (increased) active GLP-1 expression in blood serum and mimicked the effects observed by the CXXC5 knock out. However, treatment with selonsertib and ocaliva did not have any effect (FIG. 6A-6B).

Figure 7A:
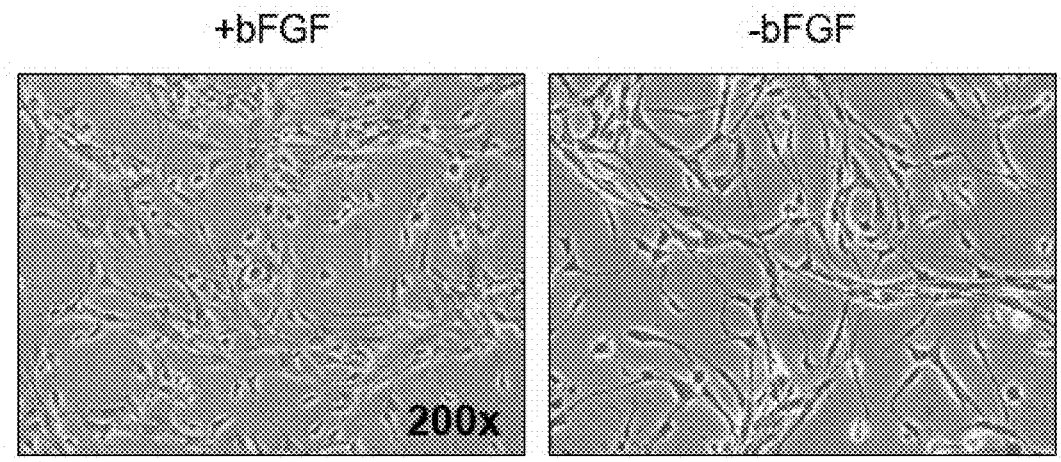
FIG. 7A. Photographs of rat neuronal stem cells (NSCs) illustrating an undifferentiated state ("+bFGF") and a differentiated state ("−bFGF"). The undifferentiated NSCs were maintained in a culture medium containing 10 ng/ml of bFGF ("+bFGF").
Figure 7B:
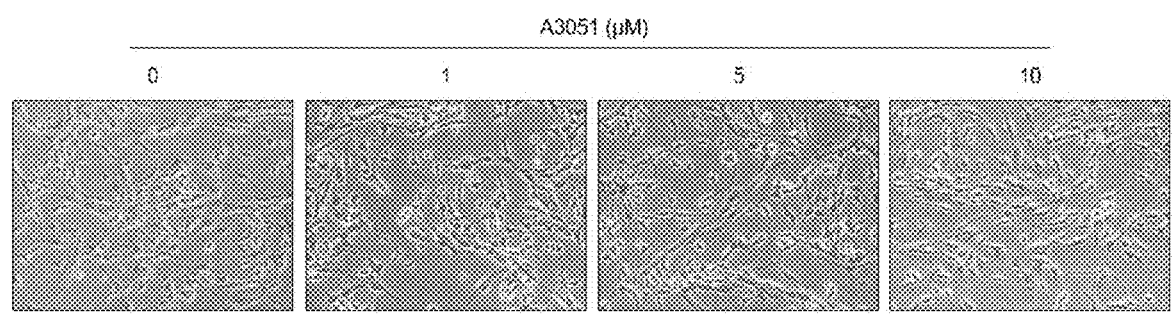
FIG. 7B. Photographs of rat neuronal stem cells (NSCs) illustrating the changes in morphology with the treatment of A3051 in various concentrations (0, 1, 5, and 10 μM). The undifferentiated NSCs were maintained in a culture medium containing 10 ng/ml of bFGF.

A3051 induced neural differentiation of the rat neuronal stem cells (NSCs). Referring now to FIG. 7A-7B, NSCs were isolated form E14 mice embryos, and maintained in the maintenance medium (supplemented) with bFGF and EGF. The neuronal differentiation was induced by treating different concentrations of A3051. Cell morphologies were captured at 24 hours after treatment of the indirubin analog 3051 using a bright-field optical microscope.

Figure 8A:
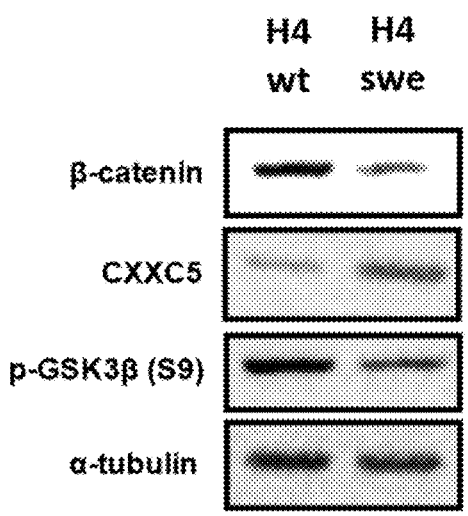
FIG. 8A. Western blots illustrating the expression of β-catenin, CXXC5 and inactivated form of GSK3β (p-GSK3β) in H4 wild-type (WT) cell (Control cell) and H4/SWE cell (APP Swedish mutant neuroglioma H4 cell line).
Figure 8B:
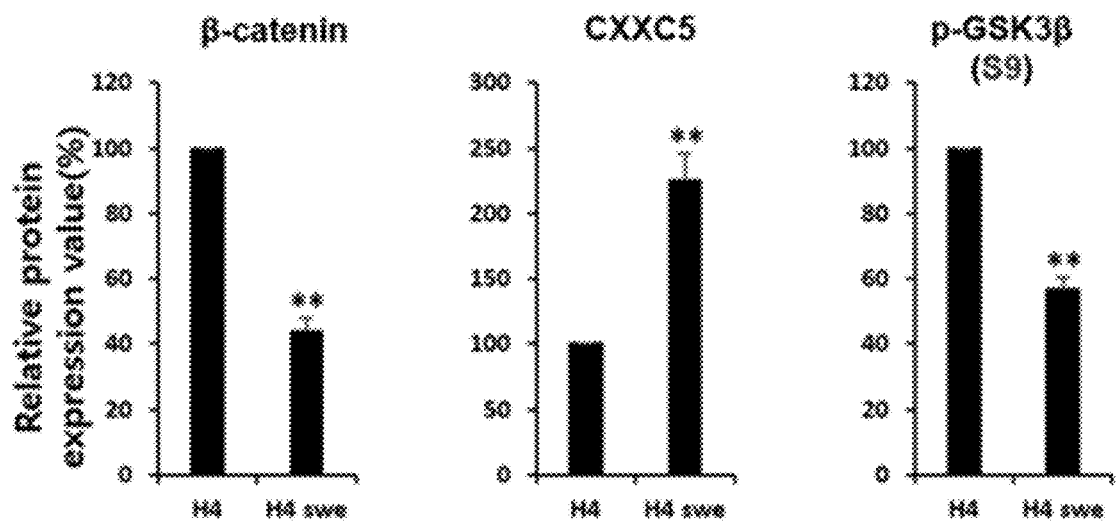
FIG. 8B. Graphs illustrating the relative expression levels of β-catenin, CXXC5 and p-GSK3β (S9) in H4 WT and H4/SWE cells.

Elevated CXXC5 levels and reduced β-catenin levels in the APP Swedish mutant neuroglioma H4 cell line. Referring now to FIG. 8A-8B, expression of CXXC5 and β-catenin was confirmed using H4/SWE cells with a Swedish mutation (K595N/M1596L) of amyloid precursor protein (APP-swe) that causes early-onset Alzheimer's disease. Western blot analyses showed that the H4/SWE cell line had lower expression levels of β-catenin, GSK3 inactive form (p-GSK3β (S9)) and higher expression level of CXXC5 than the H4 WT cell line.

Figure 9A:
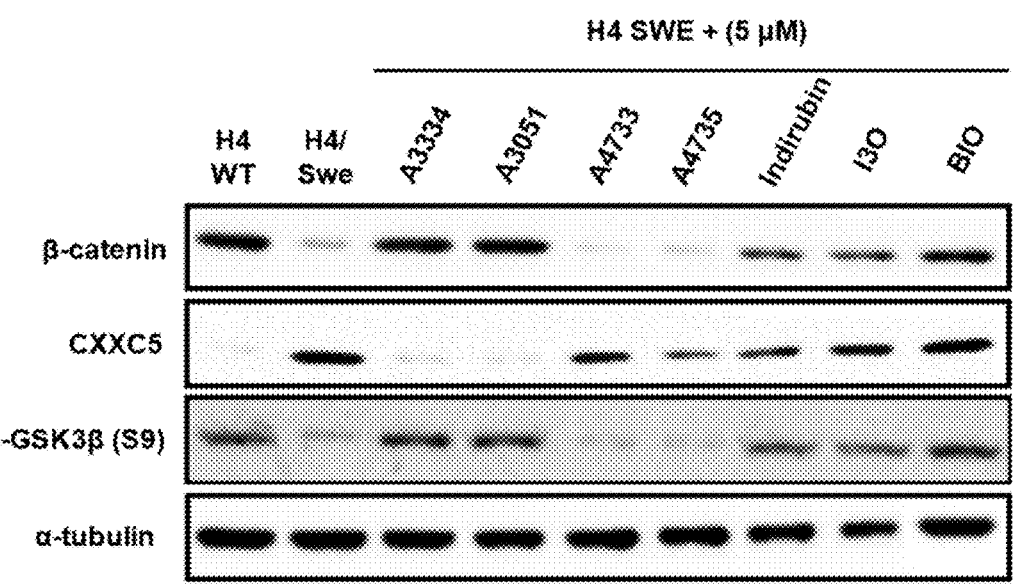
FIG. 9A. Western blots illustrating the levels of β-catenin, CXXC5 and p-GSK3β (S9) and α-tubulin in H4/SWE cells that were treated with DMSO (control), A3334, A3051, A4733, A4735, indirubin, indirubin-3'-oxime (I3O), 6-Bromoindirubin-3'-oxime (BIO) and H4 WT cells.
Figure 9B:
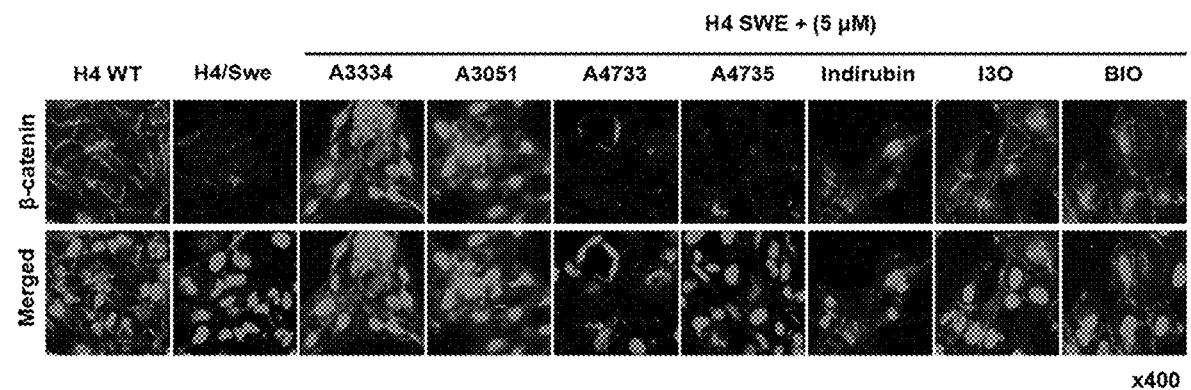
FIG. 9B. Immunocytochemical images illustrating the level and localization of β-catenin in H4/SWE cells that were treated with DMSO, A3334, A3051, A4733, A4735, indirubin, I3O, BIO and H4 WT cells. Green signal represents the expression of β-catenin and blue signal represents nuclear staining with 4',6-diamidino-2-phenylindole (DAPI).

Several indirubin analog compounds, including A3051 and A3334, increased the level and nuclear translocation of β-catenin in H4/SWE cells. Referring now to FIG. 9A-9B, H4/SWE cells showed lower β-catenin expression compared to H4 WT cells. Several compounds including A3334, A3051, indirubin, I3O, and BIO restored the level of β-catenin lowered in H4/SWE cells and increased p-GSK3β (S9) as shown by western blot analyses (FIG. 9A). A3334 and A3051 also decreased the level of CXXC5 in these cells (FIG. 9A). Immunocytochemical analyses also demonstrated that several indirubin analog compounds, especially A3334 and A3051, increased the nuclear translocation of β-catenin in H4/SWE cells (FIG. 9B).

Figure 10:
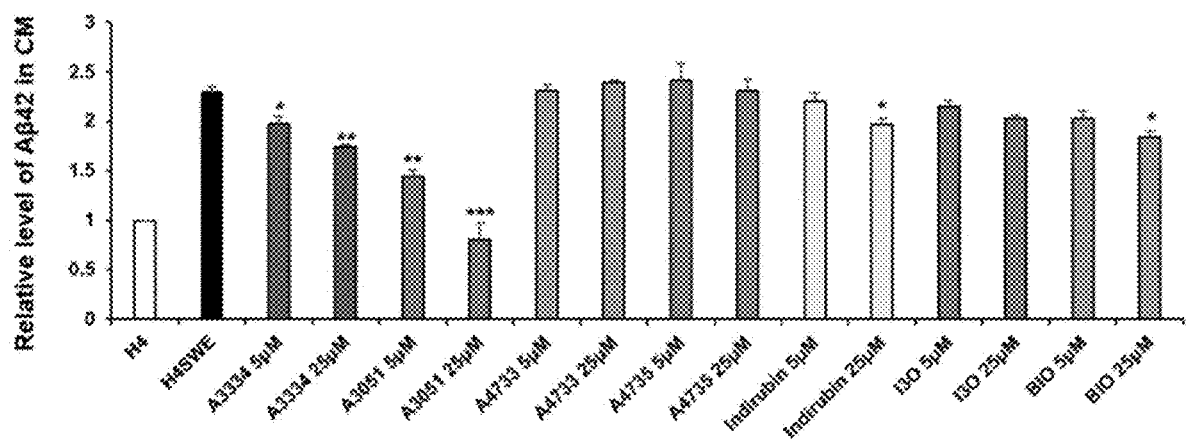
FIG. 10. Human Aβ-42 enzyme-linked immunosorbent assay (ELISA) showing the levels of secreted human amyloid β-42 in H4/SWE cells that were treated with DMSO, A3334, A3051, A4733, A4735, indirubin, I3O, BIO and H4 WT cells.

A3051 and A3334 suppressed elevated Aβ-42 secretion in H4/SWE cells. Referring now to FIG. 10, treatment with A3051 and A3334, especially A3051, inhibited the secretion of Aβ-42 in H4/SWE cells.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

We claim:

1. A method of treating a neurodegenerative disease comprising:
    administering to a subject at least one therapeutically effective dose of at least one compound or a pharmaceutically acceptable salt thereof,
    wherein the compound is:

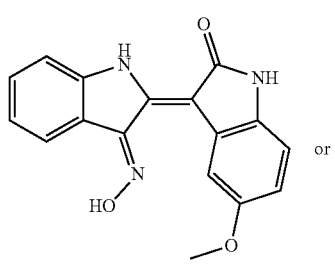

or

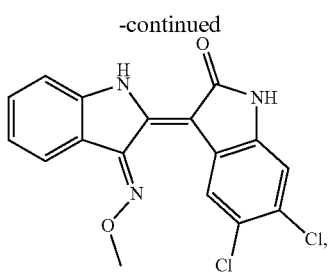

wherein the neurodegenerative diseases are Alzheimer's disease and/or Parkinson's disease.

2. The method according to claim 1, further comprising: detecting upregulated expression of CXXC5 in the subject.

3. The method according to claim 1, further comprising: identifying the subject as at risk for a neurodegenerative disease.

4. The method according to claim 1, wherein the subject exhibits abnormal GLP-1 levels, lipid profile, insulin resistance, and/or blood glucose levels.

5. The method according to claim 1, wherein the subject is diagnosed with or at risk of having dementia.

6. The method according to claim 1, wherein the at least one compound reduces and/or inhibits the CXXC5-DVL interaction.

7. The method according to claim 1, wherein the subject is a human or an animal.

8. The method according to claim 1, wherein the at least one compound is administered to the subject orally, topically, nasally, parenterally, transmucosally, transdermally, intramuscularly, intravenously, intradermally, subcutaneously, intraperitoneally, intraventricularly, intracranially, intratumorally, or by pulmonary delivery.

9. The method according to claim 1, wherein the therapeutically effective dose of the at least one compound is on the order of between: about 0.01 mg/kg to about 200 mg/kg; about 0.01 mg/kg to about 100 mg/kg; about 0.01 mg/kg to about 80 mg/kg; about 0.01 mg/kg to about 60 mg/kg; about 0.05 mg/kg to about 100 mg/kg; about 0.05 mg/kg to about 80 mg/kg; about 0.05 mg/kg to about 50 mg/kg; about 0.1 mg/kg to about 100 mg/kg; about 0.1 mg/kg to about 50 mg/kg; about 0.2 mg/kg to about 100 mg/kg; about 0.2 mg/kg to about 50 mg/kg; about 0.5 mg/kg to about 100 mg/kg; about 0.5 mg/kg to about 50 mg/kg; about 100 mg/kg to about 200 mg/kg; about 100 mg/kg to about 150 mg/kg, and/or any combination thereof.

10. The method according to claim 1, the compound is administered to the subject at least once, twice, or three times per day.

11. The method according to claim 1, wherein the subject was previously or is being concomitantly treated with at least one medication including orlistat, lorcaserin, phentermine-topiramate, naltrexone-bupropion, liraglutide, benzphetamine, diethylpropion, sulfonylureas, meglitinides, thiazolidinediones, dipeptidylpeptidase-4 (DPP-4) inhibitors, insulin analog, alpha glucosidase inhibitor, SGL T2 inhibitors, sitagliptin, metformin, rosiglitazone, ocaliva, selonsertib, elafibranol, cenicriviroc, MGL-3196, GR-MD-02, aramchol, GLP-1 analogues, and/or GLP-1 receptor agonist.

* * * * *